US 9,726,604 B2

(12) United States Patent
Sekiguchi et al.

(10) Patent No.: US 9,726,604 B2
(45) Date of Patent: Aug. 8, 2017

(54) ADHERING DETECTION APPARATUS, ADHERING SUBSTANCE DETECTION METHOD, STORAGE MEDIUM, AND DEVICE CONTROL SYSTEM FOR CONTROLLING VEHICLE-MOUNTED DEVICES

(71) Applicants: Hiroyoshi Sekiguchi, Kanagawa (JP); Shintaroh Kida, Kanagawa (JP); Kohji Oshikiri, Kanagawa (JP); Izumi Itoh, Tokyo (JP)

(72) Inventors: Hiroyoshi Sekiguchi, Kanagawa (JP); Shintaroh Kida, Kanagawa (JP); Kohji Oshikiri, Kanagawa (JP); Izumi Itoh, Tokyo (JP)

(73) Assignee: Ricoh Company, Ltd., Tokyo (JP)

( * ) Notice: Subject to any disclaimer, the term of this patent is extended or adjusted under 35 U.S.C. 154(b) by 2 days.

(21) Appl. No.: 14/924,815

(22) Filed: Oct. 28, 2015

(65) Prior Publication Data

US 2016/0131579 A1    May 12, 2016

(30) Foreign Application Priority Data

Nov. 12, 2014  (JP) .................................. 2014-229494
Jul. 6, 2015   (JP) .................................. 2015-135483

(51) Int. Cl.
   *G01N 21/55*     (2014.01)
   *B60Q 1/08*      (2006.01)
   (Continued)

(52) U.S. Cl.
   CPC ............. *G01N 21/55* (2013.01); *B60Q 1/085* (2013.01); *B60R 16/023* (2013.01);
   (Continued)

(58) Field of Classification Search
   CPC ............. G01N 21/55; G01N 2201/063; G01N 2201/061; G01N 2021/9586;
   (Continued)

(56) References Cited

U.S. PATENT DOCUMENTS 8,941,835 B2 *  1/2015  Hirai ................... G01N 21/552
                                              356/445
9,057,683 B2 *  6/2015  Itoh ......................... B60R 11/04
(Continued)

FOREIGN PATENT DOCUMENTS

EP        1507138 A2     2/2005
EP        2696195 A2     2/2014
(Continued)

OTHER PUBLICATIONS

Extended European Search Report dated Mar. 29, 2016.

*Primary Examiner* — Sang Nguyen
(74) *Attorney, Agent, or Firm* — Harness, Dickey & Pierce P.L.C.

(57)    ABSTRACT

An adhering detection apparatus includes a light source to emit probe light to a light translucent object during an emission period, and to stop an emission of the probe light to the light translucent object during a non-emission period, a light receiver to receive light coming from the light translucent object during the emission period and the non-emission period of the light source, and an adhering detection processor to perform an adhering detection processing for detecting a substance adhering to the light translucent object based on light quantity of the light coming from the light translucent object and received by the light receiver, and to output a detection result of the adhering detection processing. The adhering detection processor selectively performs one or more processes depending on the light (Continued)

quantity of the light received by the light receiver during the non-emission period of the light source.

20 Claims, 16 Drawing Sheets

(51) Int. Cl.
*B60S 1/08* (2006.01)
*B60R 16/023* (2006.01)
*G01N 21/552* (2014.01)
*G01N 21/94* (2006.01)
*G01N 21/958* (2006.01)

(52) U.S. Cl.
CPC ............ *B60S 1/0844* (2013.01); *G01N 21/94* (2013.01); *G01N 21/552* (2013.01); *G01N 2021/945* (2013.01); *G01N 2021/9586* (2013.01); *G01N 2201/061* (2013.01); *G01N 2201/063* (2013.01); *G01N 2201/064* (2013.01)

(58) Field of Classification Search
CPC ........... G01N 21/552; G01N 2021/945; G01N 2201/064; B60Q 1/085; B60R 16/023; B60S 1/0833
See application file for complete search history.

(56) References Cited

U.S. PATENT DOCUMENTS

| | | | |
|---|---|---|---|
| 2003/0156291 A1* | 8/2003 | Tsunetomo | B60S 1/0818 356/445 |
| 2005/0035926 A1* | 2/2005 | Takenaga | B60S 1/0818 345/8 |
| 2006/0043322 A1* | 3/2006 | Ishikawa | B60S 1/0822 250/573 |
| 2006/0215164 A1* | 9/2006 | Takata | B60S 1/0822 356/445 |
| 2010/0208060 A1* | 8/2010 | Kobayashi | B60S 1/0844 348/135 |
| 2013/0208120 A1 | 8/2013 | Hirai et al. | |
| 2014/0029008 A1 | 1/2014 | Hirai et al. | |
| 2014/0247357 A1 | 9/2014 | Sekiguchi | |
| 2014/0270532 A1 | 9/2014 | Sawaki et al. | |
| 2014/0303853 A1 | 10/2014 | Itoh et al. | |
| 2014/0321709 A1 | 10/2014 | Kasahara et al. | |
| 2015/0054954 A1 | 2/2015 | Itoh et al. | |
| 2015/0142263 A1 | 5/2015 | Hirai et al. | |
| 2015/0243017 A1 | 8/2015 | Fujimoto et al. | |
| 2016/0370461 A1* | 12/2016 | Sugiura | G01S 7/4817 |

FOREIGN PATENT DOCUMENTS

| | | |
|---|---|---|
| JP | 2013-117520 | 6/2013 |
| JP | 2014-032174 | 2/2015 |
| JP | 2005-195566 | 7/2015 |
| WO | WO-2013065868 A1 | 5/2013 |

* cited by examiner

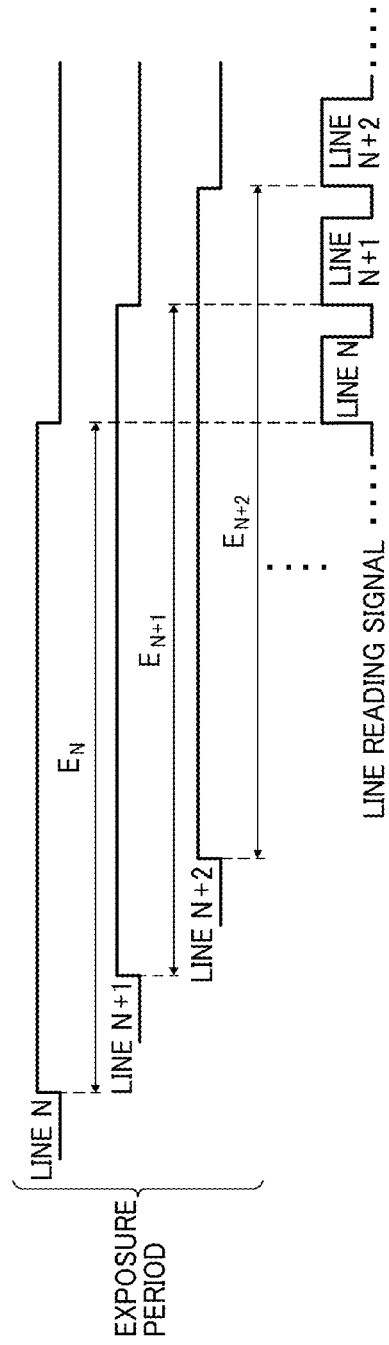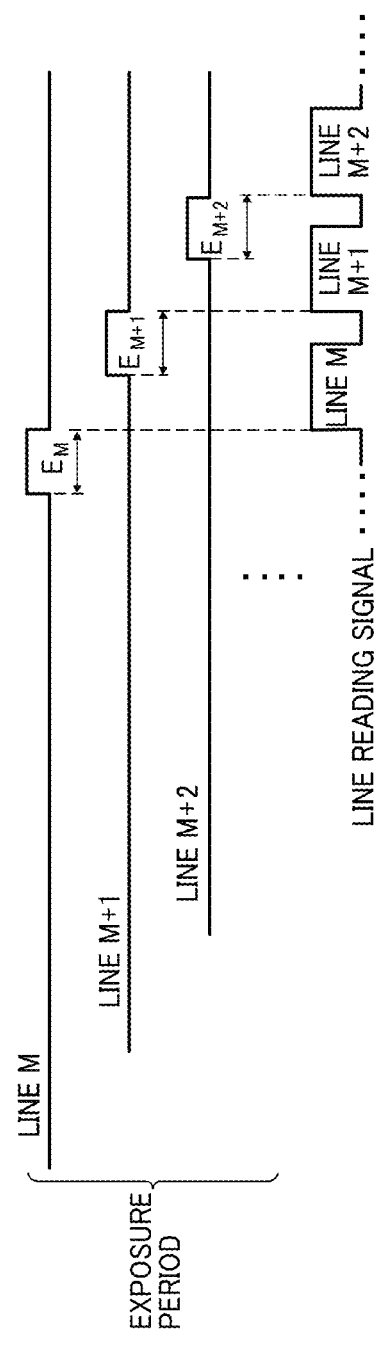

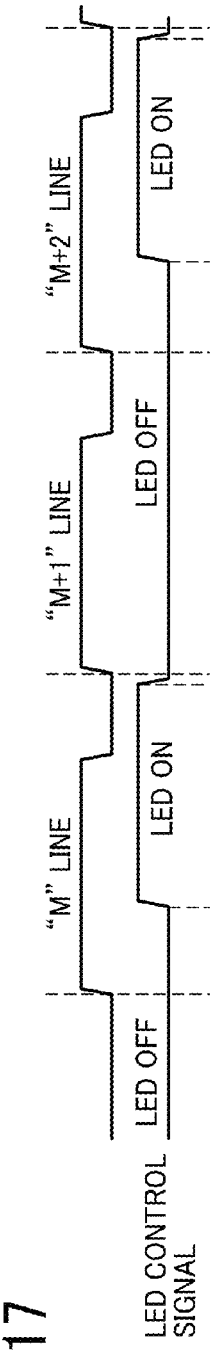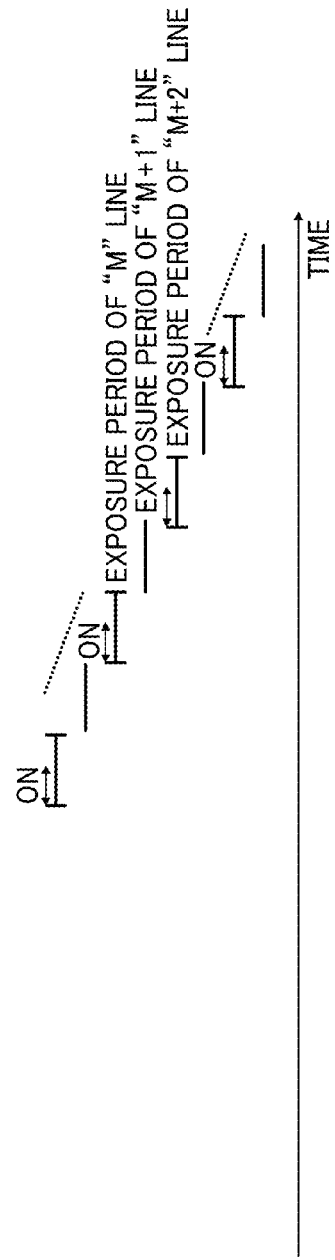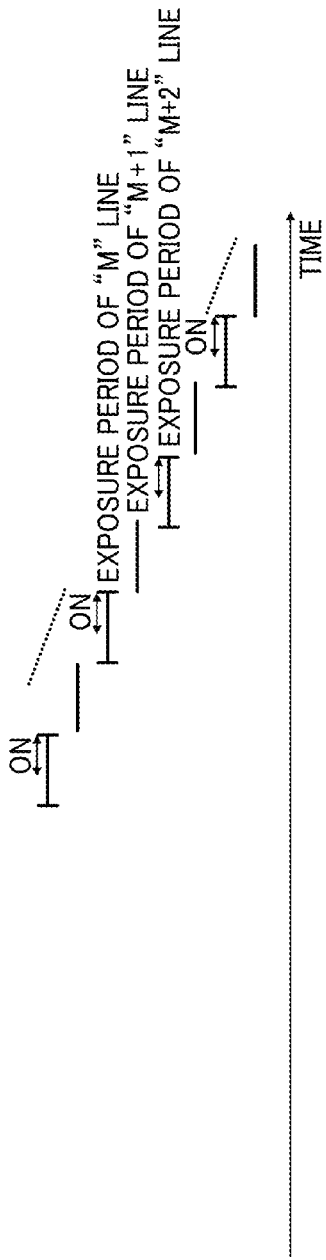
FIG. 17
FIG. 18
FIG. 19

ADHERING DETECTION APPARATUS, ADHERING SUBSTANCE DETECTION METHOD, STORAGE MEDIUM, AND DEVICE CONTROL SYSTEM FOR CONTROLLING VEHICLE-MOUNTED DEVICES

CROSS-REFERENCE TO RELATED APPLICATION

This application claims priority pursuant to 35 U.S.C. §119(a) to Japanese Patent Application Nos. 2014-229494, filed on Nov. 12, 2014 and 2015-135483, filed on Jul. 6, 2015 in the Japan Patent Office, the disclosure of which are incorporated by reference herein in their entirety.

BACKGROUND

Technical Field

The present invention relates to an adhering detection apparatus, adhering detection method, a storage medium, and a device control system for controlling vehicle-mounted devices.

Background Art

Conventional adhering detection apparatuses including a light source and a light receiver are used to detect substances adhering to a light translucent object such as windshield made of glass, in which light emitted from the light source is irradiated to the light translucent object, and light coming from the light translucent object such as reflection light is received by the light receiver, and then substance adhering to the light translucent object is detected based on light quantity of the light received by the light receiver.

For example, conventional arts disclose an raindrop detection apparatus to detect raindrop adhering to a windshield of automobile, in which light emitted from the light source is irradiated to the windshield, and reflection light reflected from the windshield is received by a raindrop detection portion of an image sensor to capture an image, with which raindrops adhering to the windshield is detected. As to this raindrop detection apparatus, raindrops can be detected based on difference information between a light-ON image captured when the light source is emitting light (emission period) and a light-OFF image captured when the light source is not emitting the light (non-emission period). Since the detection precision of raindrop is decreased by ambient light other than the light emitted from the light source, the effect of ambient light is required to be suppressed, which means the ambient light becomes noise that disrupts the raindrop detection. Since the light-OFF image is an image generated only from the ambient light, the difference information which can be obtained by subtracting the light-OFF image from the light-ON image becomes information excluding the ambient light component from the light-ON image. By performing the raindrop detection based on this difference information, the raindrop detection processing having reduced the effect of the ambient light can be performed.

However, the effect of ambient light cannot be removed completely even if the detection of adhering substance such as raindrop is performed based on the above mentioned difference information. Specifically, remaining amount of the ambient light component in the difference information causes error to the adhering substance detection process. Further, the remaining amount of the ambient light varies depending on image capturing conditions, and has greater fluctuation. Therefore, detection results of the adhering substance have greater fluctuation, and such fluctuated detection results cause various problems at the later stage processing.

The fluctuated detection results also occur to adhering detection apparatuses including a light source and a light receiver for detecting a substance adhering to a light translucent object such as glass, in which light emitted from the light source is irradiated to the light translucent object, and light coming from the light translucent object such as reflection light is received by the light receiver, and then the substance adhering to the light translucent object is detected based on light quantity received by the light receiver. Therefore, the fluctuation of the detection results may occur to the adhering detection processing using the difference information, and also the adhering detection processing using only light quantity of the light received by the light receiver during an emission period of the light source.

SUMMARY

In one aspect of the present invention, an adhering detection apparatus is devised. The adhering detection apparatus includes a light source to emit probe light to a light translucent object during an emission period, and to stop an emission of the probe light to the light translucent object during a non-emission period, a light receiver to receive light coming from the light translucent object during the emission period and the non-emission period of the light source, and an adhering detection processor to perform an adhering detection processing for detecting a substance adhering to the light translucent object based on light quantity of the light coming from the light translucent object and received by the light receiver, and to output a detection result of the adhering detection processing. The adhering detection processor selectively performs one or more processes depending on the light quantity of the light received by the light receiver during the non-emission period of the light source.

In another aspect of the present invention, a method of detecting a substance adhering to a light translucent object is devised. The method includes the steps of emitting probe light from a light source to the light translucent object during an emission period of the light source and to stop emitting the probe light from the light source during a non-emission period, receiving light coming from the light translucent object by a light receiver during the emission period and the non-emission period, detecting a substance adhering to the light translucent object based on a light quantity of the light received by the light receiver at the receiving step, outputting a detection result obtained at the detecting step, and selectively performing one or more processes depending on the light quantity of the light received by the light receiver during the non-emission period of the light source.

In another aspect of the present invention, a non-transitory computer-readable storage medium storing a program that, when executed by a computer, causes the computer to execute a method of detecting a substance adhering to a light translucent object by using an adhering detection apparatus is devised. The method includes the steps of emitting probe light from a light source to the light translucent object during an emission period of the light source and to stop emitting the probe light from the light source during a non-emission period, receiving light coming from the light translucent object by a light receiver during the emission period and the non-emission period, detecting a substance adhering to the light translucent object based on a light quantity of the light received by the light receiver at the receiving step, outputting a detection result obtained at the detecting step, and selectively performing one or more processes depending on the light quantity of the light received by the light receiver during the non-emission period of the light source.

BRIEF DESCRIPTION OF THE DRAWINGS

A more complete appreciation of the disclosure and many of the attendant advantages and features thereof can be readily obtained and understood from the following detailed description with reference to the accompanying drawings, wherein:

FIG. 16A indicates a relationship of data reading timing and exposure period for sensing frames employing a rolling shutter method;

FIG. 16B indicates a relationship of data reading timing and exposure period for raindrop detection frames employing a rolling shutter method;

FIG. 17 is an example of a timing chart of line reading signals for the raindrop detection frame and light emission timing of the light source;

FIG. 18 is an example of a light emission timing of the light source during an exposure period of each line;

FIG. 19 is another example of a light emission timing of the light source during an exposure period of each line;

Figure 1:
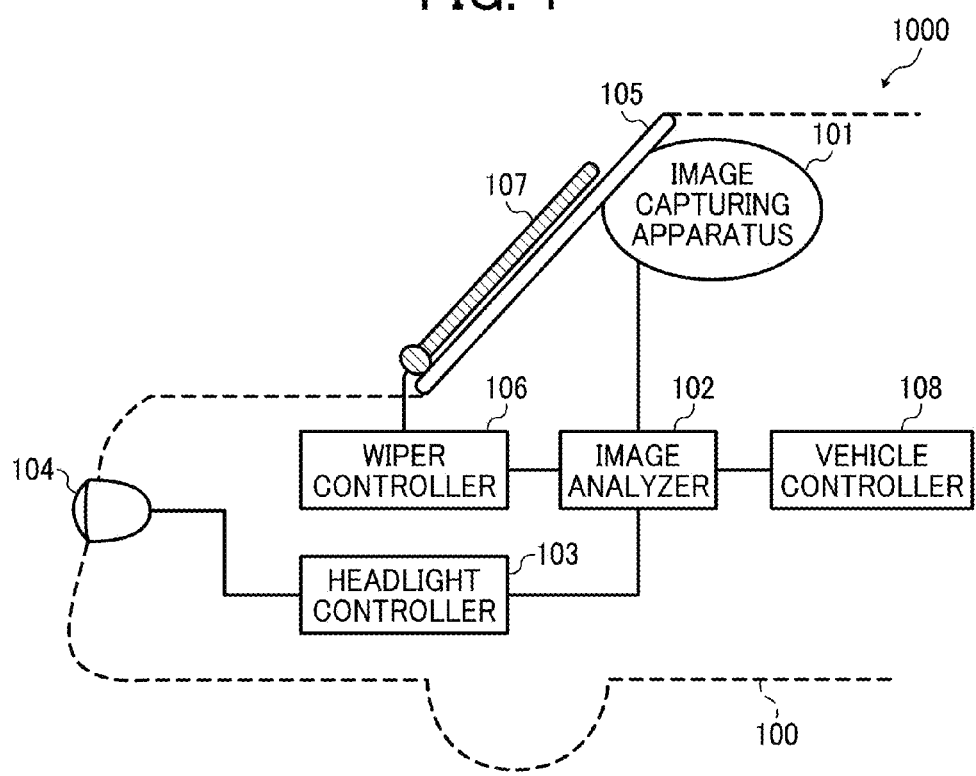
FIG. 1 illustrates a schematic configuration of a device control system for controlling vehicle-mounted devices according to a first example embodiment.

The accompanying drawings are intended to depict exemplary embodiments of the present invention and should not be interpreted to limit the scope thereof. The accompanying drawings are not to be considered as drawn to scale unless explicitly noted, and identical or similar reference numerals designate identical or similar components throughout the several views.

DETAILED DESCRIPTION

A description is now given of exemplary embodiments of the present invention. It should be noted that although such terms as first, second, etc. may be used herein to describe various elements, components, regions, layers and/or sections, it should be understood that such elements, components, regions, layers and/or sections are not limited thereby because such terms are relative, that is, used only to distinguish one element, component, region, layer or section from another region, layer or section. Thus, for example, a first element, component, region, layer or section discussed below could be termed a second element, component, region, layer or section without departing from the teachings of the present invention.

In addition, it should be noted that the terminology used herein is for the purpose of describing particular embodiments only and is not intended to be limiting of the present invention. Thus, for example, as used herein, the singular forms "a", "an" and "the" are intended to include the plural forms as well, unless the context clearly indicates otherwise. Moreover, the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Furthermore, although in describing views illustrated in the drawings, specific terminology is employed for the sake of clarity, the present disclosure is not limited to the specific terminology so selected and it is to be understood that each specific element includes all technical equivalents that operate in a similar manner and achieve a similar result. Referring now to the drawings, one or more apparatuses or systems according to one or more example embodiments are described hereinafter.

(First Example Embodiment)

A description is given of a device control system for controlling vehicle-mounted devices that employs an adhering detection apparatus according to a first example embodiment of the present invention, in which the device control system employing the adhering detection apparatus is mounted, for example, in a vehicle. Hereinafter, the device control system for controlling vehicle-mounted devices may be referred to as the "device control system" for the simplicity of the expression. The adhering detection apparatus can be used with the device control system, but the adhering detection apparatus can be applied for other systems to detect objects adhering to a light translucent member. The vehicle may not be limited to any specific vehicles but includes various types of vehicles such as automobiles, ships, robots or the like. The adhering detection apparatus may also be referred to the adhering substance detection apparatus. Further, the adhering detection apparatus to detect objects adhering to the light translucent object can be applied any apparatuses other than the vehicles such as monitoring cameras.

FIG. 1 illustrates a schematic configuration of a device control system 1000 for controlling vehicle-mounted devices according to a first example embodiment of the present invention. A vehicle 100 such as an automobile includes the device control system for controlling vehicle-mounted devices, and an image capturing apparatus. In this disclosure, the vehicle 100 is explained as an example of movable apparatuses equipped with the device control system. The device control system can be applied to any types of movable apparatuses used under various environment. The image capturing apparatus can capture images in an area around the vehicle 100 such as an area ahead of the vehicle 100 as captured image data. Based on the captured image data, the device control system 1000 can perform light control of headlight, wiper-drive control, and a control of other devices mounted in the vehicle 100.

As illustrated in FIG. 1, the device control system 1000 includes, for example, an image capturing apparatus 101 having an image capture device 200 (FIG. 2), an image analyzer 102, a vehicle controller 108, a wiper controller 106, and a headlight controller 103. Each of the vehicle controller 108, the wiper controller 106, and the headlight controller 103 can be used as a controller to control various devices mounted in the vehicle 100.

The image capture device 200 used for the device control system 1000 can be disposed in the image capturing apparatus 101. The image capture device 200 captures, for example, views of a front-area of the vehicle 100, wherein the front-area may be referred to as an image capturing area or captured image area. For example, the image capture device 200 captures views of the front-area of the vehicle 100 when the vehicle 100 is running. The image capture device 200 may be, for example, disposed near a rear-view mirror disposed near a windshield 105 of the vehicle 100. Image data captured by the image capture device 200 of the image capturing apparatus 101 is input to the image analyzer 102.

The image analyzer 102 analyzes the captured image data, transmitted from the image capture device 200, in which the image analyzer 102 can be used to compute information of other vehicles existing in a front direction of the vehicle 100 such as positions of other vehicles, a point of the compass (e.g., north, south, east, west) and distance to other vehicles. Further, the image analyzer 102 can be used to detect a substance such as raindrops, foreign particles, or the like adhering to the windshield 105. Further, the image analyzer 102 can be used to detect a detection-target object existing on road surfaces such as a lane (e.g., white line) or the like from the image capturing area. Further, the image analyzer 102 can be used to detect other vehicles. Further, the image analyzer 102 can be used to compute an amount of rain. Specifically, by recognizing tail lamps of other vehicles, the image analyzer 102 can detect a front-running vehicle (or ahead vehicle) running in front of the vehicle 100 in the same running direction, and by recognizing headlights of other vehicles, the image analyzer 102 can detect an oncoming vehicle coming toward the vehicle 100 such as head-to-head direction.

The computation result of the image analyzer 102 can be transmitted to the headlight controller 103. For example, the headlight controller 103 generates control signals to control a headlight 104 based on distance data computed by the image analyzer 102, wherein the headlight 104 is one of devices mounted in the vehicle 100. Specifically, a switching control of high beam/low beam of the headlight 104 is performed, and a light-dimming control is partially performed for the headlight 104 to prevent a projection of high intensity light of headlight of the vehicle 100 to eyes of drivers of front-running vehicles and oncoming vehicles, by which the drivers of other vehicles are not dazzled by light coming from the headlight of the vehicle 100 while providing the enough field of view for the driver of vehicle 100.

The computation result of the image analyzer 102 is also transmitted to the wiper controller 106. The wiper controller 106 controls a wiper 107, which is one of devices mounted in the vehicle 100, to remove substance such as raindrops, foreign particles, or the like adhering to the windshield 105. The wiper controller 106 generates control signals to control the wiper 107 upon receiving the detection result of adhering substances or foreign particles from the image analyzer 102. When the control signals generated by the wiper controller 106 are transmitted to the wiper 107, the wiper 107 is activated to securely provide the field of view for the driver of the vehicle 100.

Further, the computation result of the image analyzer 102 is also transmitted to a vehicle controller 108, which controls the driving of the vehicle 100. If the vehicle 100 deviates or departs from the vehicle lane, defined by the lane (e.g., white line), based on the detection result of the lane detected by the image analyzer 102, the vehicle controller 108 activates an alarm or warning to the driver of the vehicle 100, and activates a cruise device control system such as controlling of a steering wheel and/or brake of the vehicle 100 to keep the vehicle 100 in the vehicle lane.

Figure 2:
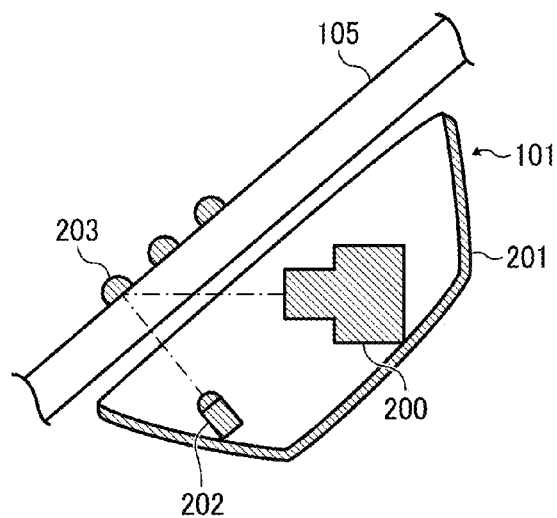
FIG. 2 illustrates a schematic configuration of an image capturing apparatus of the device control system of FIG. 1.
Figure 3A:
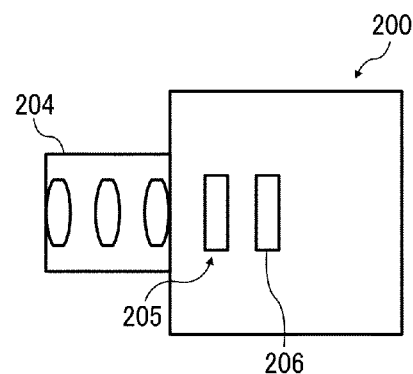
FIG. 3A illustrates a schematic configuration of an image capture device disposed in the image capturing apparatus.

FIG. 2 illustrates a schematic configuration of the image capturing apparatus 101, and FIG. 3A illustrates a schematic configuration of the image capture device 200 disposed in the image capturing apparatus 101. As illustrated in FIG. 2, the image capturing apparatus 101 includes, for example, the image capture device 200, a light source 202, and a casing 201 that encases the image capture device 200 and the light source 202. The image capturing apparatus 101 can be attached to an interior side of the windshield 105 of the vehicle 100. As illustrated in FIG. 3A, the image capture device 200 includes, for example, a capture lens 204, an optical filter 205, and an image sensor 206. The optical filter 205 may include a front-end filter and a rear-end filter. The light source 202 emits light toward the windshield 105, and the light reflected at the outer face of the windshield 105 (i.e., reflection light) can enter the image capture device 200.

Figure 3B:
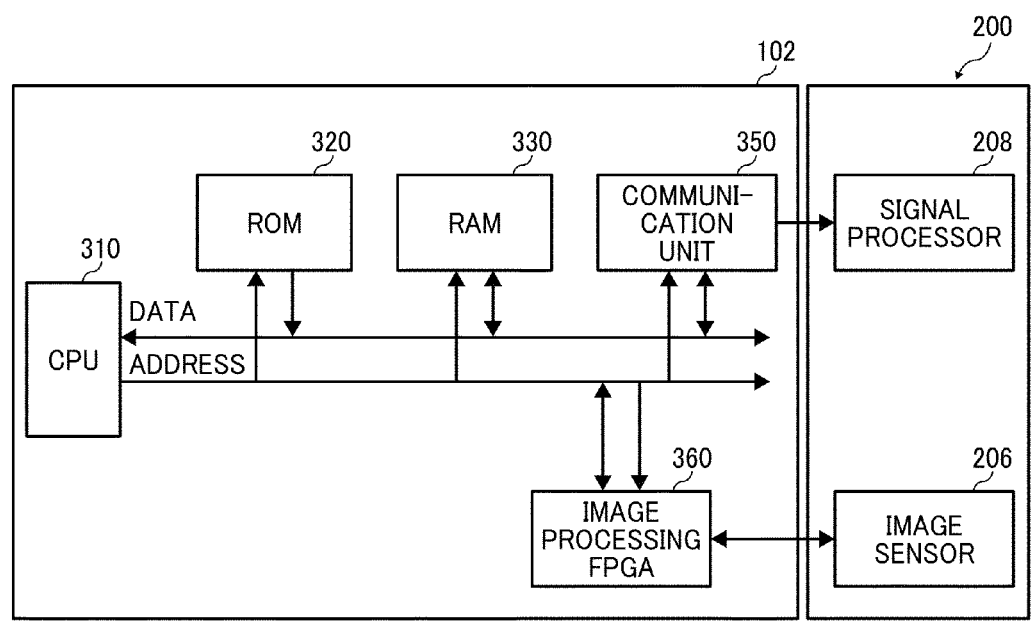
FIG. 3B is an example of a hardware configuration of an image analyzer.

FIG. 3B is an example of a hardware configuration of the image analyzer 102. The image analyzer 102 includes, for example, a central processing unit (CPU) 310, a read only memory (ROM) 320, a random access memory (RAM) 330, a communication unit 350, and an image processing field programmable gate array (FPGA) 360. The ROM 320 stores programs executable by the CPU 310. The RAM 330 is used as a working memory when executing the programs. The communication unit 350 is used to communicate with a signal processor 208 (see FIG. 10) such as transmitting a recognition result to the signal processor 208. The image processing FPGA 360 processes image data acquired by the image sensor 206. The image analyzer 102 can be implemented by using the image processing FPGA 360 programmed using programs and data stored in the ROM 320. The image analyzer 102 can be devised as a hardware or a combination of software and hardware. Specifically, image data acquired by the image sensor 206 can be processed by the CPU 310 that executes the programs stored in the RAM 330, or can be processed by the image processing FPGA 360 programmed using the programs. The frame determination can be performed by the image processing FPGA 360 or CPU 310. Specifically, the image processing FPGA 360 or CPU 310 performs the frame determination and exposure time control, in which frame numbers are assigned to given pixels composing an image, and the exposure time of the image sensor 206 corresponding to each of the frame numbers is controlled.

In the first example embodiment, the light source 202 emits light used for detecting substances such as raindrops adhering to the outer face of the windshield 105. Hereinafter, such substances may be referred to as a substance, adhered substance, adhering substance, or raindrop, as required. In this description, raindrop is used as an example of substance adhering to the outer face of the windshield 105. If a raindrop 203 adheres on the outer face of the windshield 105 as illustrated in FIG. 2, light emitted from the light source 202 reflects at a boundary face between the raindrop 203 and the outer face of the windshield 105, and the reflected light enters the image capture device 200. Based on the image data captured by the image capture device 200, the raindrop 203 adhering to the windshield 105 can be detected. In the one or more example embodiments of the present invention, the light emitted from the light source 202 can be used as probe light to detect substances adhering to the outer face of the windshield 105, which is an example of a light translucent object or member.

Further, as illustrated in FIG. 2, the casing 201 of the image capturing apparatus 101 and the windshield 105 encases the image capture device 200 and the light source 202. With this encasing configuration by using the casing 201, even if fogging occurs on the inner face of the windshield 105, fogging may not occur to a part of the windshield 105 encased by the casing 201 of the image capturing apparatus 101. Therefore, an analysis failure by the image analyzer 102 due to the fogging of the windshield 105 can be prevented, and thereby various control operations can be effectively performed based on the analysis result of the image analyzer 102.

Further, the fogging of the windshield 105 may be used to control an air-conditioning system of the vehicle 100, in which the fogging of the windshield 105 can be detected using image data captured by the image capture device 200.

In such a case, an air-flow path is formed at a part of the casing 201 so that a part of the windshield 105 facing the image capture device 200 has a same condition with other parts.

In the first example embodiment, a focus position of the capture lens 204 can be set infinity, or at positions between infinity and the windshield 105. With this setting, the detection of the raindrop 203 on the windshield 105, the detection of the front-running vehicle and the oncoming vehicle, and the detection of the lane (e.g., white line) can be performed by obtaining suitable information from the image data captured by the image capture device 200.

For example, the raindrop 203 adhering to the windshield 105 can be detected as follows. Typically, an image of a raindrop, captured as image data, is observed as a circle shape. Therefore, when to recognize a candidate raindrop image as a raindrop image (i.e., shape recognition processing), it is determined whether the candidate raindrop image in the captured image data has a circle shape. The shape recognition processing can be effectively performed by setting the focus of the capture lens 204 at infinity, or between infinity and the windshield 105 rather than setting the focus of the capture lens 204 at the raindrop 203 on the outer face of the windshield 105. If the focus of the capture lens 204 is set at infinity, or between infinity and the windshield 105, the image can be captured with a given level of out-of-focused or defocused condition, with which shape recognition performance of raindrop such as recognizing the raindrop as a circle shape can be enhanced, and thereby the raindrop detection performance can be enhanced.

Figure 4:
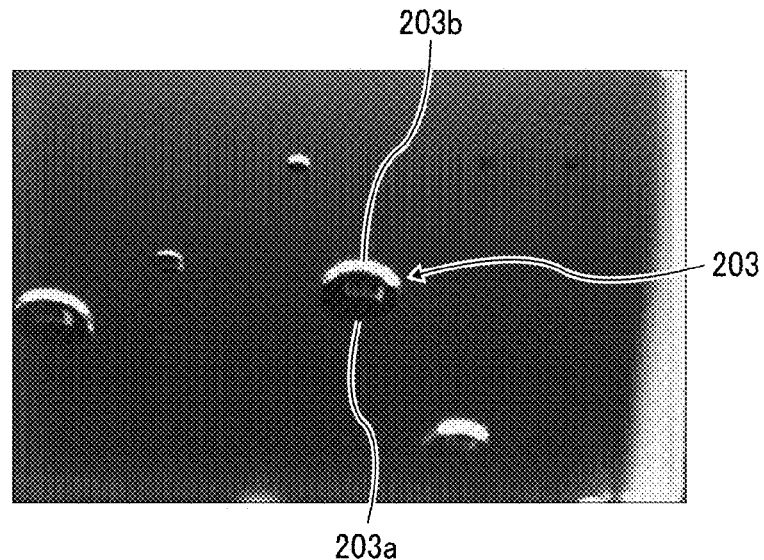
FIG. 4 shows infrared image data, which is captured as image data for raindrop detection, in which the focus of a capture lens is set at a raindrop on an outer face of a windshield.
Figure 5:
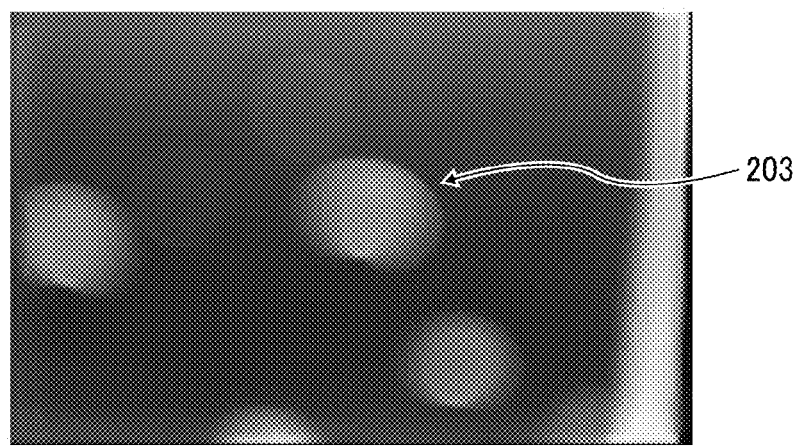
FIG. 5 shows another infrared image data, which is captured as image data for raindrop detection, in which the focus of the capture lens is set at infinity.

FIG. 4 shows infrared image data, which is captured as image data for the raindrop detection, in which the focus of the capture lens 204 is set at the raindrop 203 on the outer face of the windshield 105. FIG. 5 shows another infrared image data, which is captured as image data for the raindrop detection, in which the focus of the capture lens 204 is set at infinity. When the focus of the capture lens 204 is set at the raindrop 203 on the outer face of the windshield 105, a raindrop image may be captured with a background image 203a being projected on a raindrop as shown in FIG. 4. The background image 203a may cause a detection malfunction of the raindrop 203. Further, as shown in FIG. 4, a raindrop boundary 203b, which is a part of raindrop, may become an arc-like shape having a greater intensity. A shape of the raindrop image having such having greater intensity changes depending on the direction of sun light and/or position of streetlamp, in which the shape of raindrop image changes in various patterns. If the shape recognition processing is required to handle such various patterns, the processing load becomes great, and further, the recognition precision may deteriorate.

By contrast, when the focus of the capture lens 204 is set at infinity as shown in FIG. 5, an image is captured with a given level of out-of-focused or defocused condition. Therefore, a ghost image of the background image 203a is not projected or included in the captured image data, and thereby the detection malfunction of the raindrop 203 can be reduced. Further, the shape of images of out-of-focused condition may not change greatly even if the direction of sun light and/or the position of streetlamp changes, and thereby the shape of raindrop image does not change greatly, which means the shape of raindrop image can be recognized substantially as a circle shape. Therefore, the processing load of the shape recognition processing for the raindrop 203 can be reduced, and further the recognition precision can be enhanced.

However, if the focus of the capture lens 204 is set at infinity, a tail lamp of the front-running vehicle running at a far distance ahead of the vehicle 100 may be recognized by one or so light receiving elements of the image sensor 206, which means the tail lamp light is received by the one or so light receiving elements. In such a case, the tail lamp light may not be received by a red-light receiving element disposed for receiving the tail lamp color such as red, by which the tail lamp cannot be recognized, and thereby the front-running vehicle cannot be detected. To avoid such situation, the focus of the capture lens 204 is not set at infinity, but preferably set at a point closer to the vehicle 100 compared to infinity. With this setting, the tail lamp of the front-running vehicle running at a far distance ahead of the vehicle 100 can be recognized as an image having out-of-focused or defocused condition, by which the number of the light receiving elements that can receive the light of tail lamp can be increased. Therefore, the recognition precision of the tail lamp can be enhanced, and thereby the detection precision of the front-running vehicle at a far distance ahead of the vehicle 100 can be enhanced.

The light source 202 of the image capturing apparatus 101 can employ, for example, a light emitting diode (LED), a semiconductor laser such as laser diode (LD), or the like. Further, the wavelength of emission light of the light source 202 can employ, for example, visible light, infrared light, or the like. However, the visible light emitted from the light source 202 may cause dazzling of drivers of the oncoming vehicle and pedestrians. Such dazzling can be avoided using light having a wavelength longer than the wavelength of visible light and effectively receivable within the light sensitivity of the image sensor 206. For example, the wavelength of the infrared light having a wavelength range from 800 nm to 1000 nm can be used. In the first example embodiment, the light source 202 emits the light having a wavelength range of the infrared light.

When the image capture device 200 captures the infrared light reflected from the windshield 105, the image sensor 206 of the image capture device 200 receives the infrared light emitted from the light source 202 and then reflected from the windshield 105, and also ambient light having greater light intensity such as sun light including infrared light. To reduce the effect of the ambient light having greater light intensity to the infrared light originally coming from the light source 202, the light emission quantity of the light source 202 may be set greater than the light emission quantity of the ambient light. However, it is difficult to devise the light source 202 having the greater light emission quantity.

Figure 6:
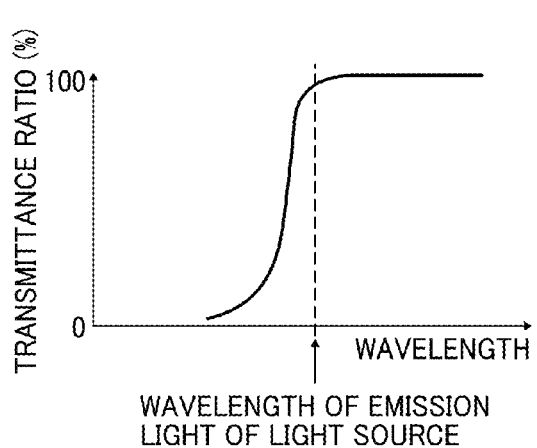
FIG. 6 is an example of a cut-filter that cuts light having a wavelength smaller than a wavelength of emission light of a light source.
Figure 7:
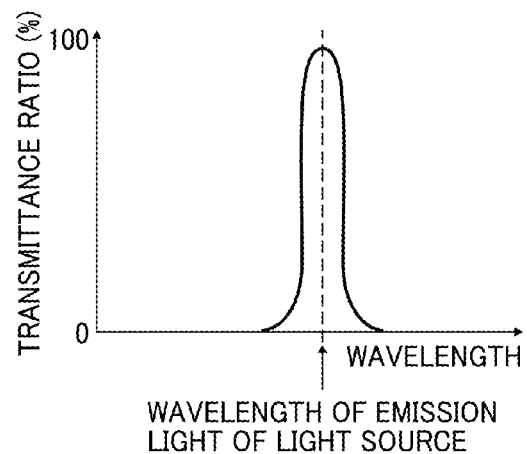
FIG. 7 is an example of a band-pass filter that has a peak of transmittance ratio of light substantially matched to a specific wavelength of light of the light source.

In view of such problem, in the first example embodiment, for example, a suitable cut-filter or a band-pass filter may be used. As illustrated in FIG. 6, a cut-filter that cuts light having a wavelength smaller than a wavelength of emission light of the light source 202 can be used. Further, as illustrated in FIG. 7, a band-pass filter that has a peak of transmittance ratio of light substantially matched to a specific wavelength of light of the light source 202 can be used. With this configuration, the image sensor 206 can effectively receive light emitted from the light source 202 using such filters. By using such filters, the light having a wavelength, which is other than the wavelength of emission light originally emitted from the light source 202, can be removed. Therefore, the image sensor 206 can receive the light emitted from the light source 202 with the quantity relatively greater than the ambient light. Therefore, without using the light source 202 having greater light emission intensity, the light originally emitted from the light source 202 can be effectively received by the image sensor 206 while reducing the effect of the ambient light.

However, as to the first example embodiment, the raindrop 203 on the windshield 105 is detected based on the captured image data, and further the front-running vehicle and the oncoming vehicle, and the lane (e.g., white line) are also detected based on the captured image data. Therefore, if the light having a given wavelength range, which is other than a wavelength of infrared light emitted from the light source 202, is removed from an entire image, the image sensor 206 cannot receive light having the given wavelength range used for detecting the front-running vehicle/oncoming vehicle and the lane, by which the detection of vehicle/oncoming vehicle and the lane cannot be performed effectively.

In view of such issue, in the first example embodiment, an image area of captured image data is segmented into one detection image area used as a raindrop detection image area, and another detection image area used as a vehicle detection image area. The raindrop detection image area can be used to detect the raindrop 203 on the windshield 105. The vehicle detection image area can be used to detect the front-running vehicle/oncoming vehicle, and the lane (e.g., white line). Therefore, the optical filter 205 is disposed of a sub-filter (hereinafter, raindrop detection filter) that can remove light having a given wavelength band, which is other than infrared light emitted from the light source 202, and the raindrop detection filter is disposed only for the raindrop detection image area. In this configuration, the raindrop detection image area is used to capture image data by disposing the raindrop detection filter, and the vehicle detection image area is used to capture image data without disposing the raindrop detection filter.

Figure 8A:
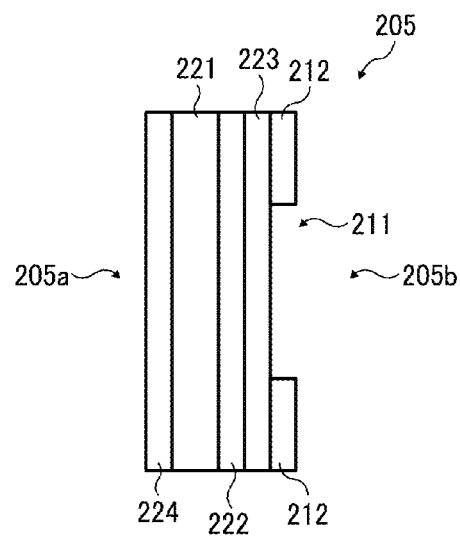
FIG. 8A is a cross-sectional view of an optical filter disposed in the image capture device.

FIG. 8A is a cross-sectional view of the optical filter 205. As illustrated in FIG. 8A, the optical filter 205 includes, for example, a base 221, a spectral filter layer 224, a polarizing filter layer 222, a spin-on-glass (SOG) layer 223, and an infrared transmission filter 212, in which the spectral filter layer 224 is formed on the base 221 at a side 205a (closer to the capture lens 204) to pass through infrared light and visible light, and the polarizing filter layer 222, the SOG layer 223, and the infrared transmission filter 212 (raindrop detection filter) are formed on the base 221 at a side 205b (closer to the image sensor 206). The infrared transmission filter 212 is employed as an example of a wavelength selection filter.

With employing this configuration forming the filter layers of the optical filter 205 on both faces of the base 221, warping of the optical filter 205 can be reduced, in particular prevented. If these multi-layers are formed on only one face side of the base 221, stress occurs and then warping occurs. However, when the multi-layers are formed on the both faces of the base 221 as illustrated in FIG. 8A, stress occurring to one side can be compensated by stress occurring to the opposite side, with which the warping can be reduced, in particular prevented.

The base 221 is made of translucent material such as glass, sapphire, rock crystal, which can pass through light such as visible light and infrared light. As to the first example embodiment, the base 221 can be made of glass having high durability with reasonable cost such as vitreous silica, silica glass, quartz glass, fused silica (refractive index of 1.46), heat resistant glass (refractive index of 1.51) such as Tempax (registered trademark) glass or the like.

The spectral filter layer 224, formed at the side 205a of the base 221, is a filter that can pass through a wavelength window of from 400 nm to 670 nm (visible light range) and a wavelength window from 940 nm to 970 nm (infrared light range). The visible light is used to detect information around the vehicle, and the infrared light is used to detect raindrops. Further, the spectral filter layer 224 does not substantially pass through a wavelength window from 700 nm to 940 nm. For example, transmittance of the spectral filter layer 224 is preferably designed to five (5) percent or less for 700 nm to 940 nm because if the light having the wavelength window from 700 nm to 940 nm is included in the received image data, obtained image data becomes red as whole, and it becomes difficult to extract a red portion such as a tail lamp and red-color signs. Therefore, if an infrared cut-filter is formed, other color light that becomes disturbing light can be removed, with which the recognition or detection precision of the tail lamp can be enhanced.

Further, the polarizing filter layer 222, formed at the side 205b of the base 221, can cut S-polarized light and pass only P-polarized light. By disposing the polarizing filter layer 222, disturbance factors and unnecessary reflection light (ghost light) can be cut.

As to the first example embodiment, the polarizing filter layer 222 is a polarizer having a wire grid structure. The wire grid structure is formed by disposing a number of conductive metal wires with a given wire pitch along a given direction. For example, a number of the aluminum wires can be arranged with a given wire pitch along a given direction. By setting the wire pitch of the wire grid structure enough smaller than a wavelength band of the incidence light (e.g., visible light having wavelength of 400 nm to 800 nm) such as one half (½) or less of the wavelength of the incidence light, electric field vectors of light oscillating in parallel to the long side direction of metal wire can be mostly reflected, and electric field vectors of light oscillating in perpendicular to the long side direction of metal wire can be mostly passed through, by which the polarizer that can generate single polarization light can be produced.

When the wire grid polarizer is used, it should be noted that the light diminishing ratio increases when the area of cross section of the metal wire increases. Further, when the metal wire has a thickness, which is too great compared to a given interval pitch, the passing ratio of light decreases. Further, if the shape of cross section of the metal wire, perpendicular to the long direction of the metal wire, is a taper shape, the light passing ratio and wavelength dispensability of polarized light become small in a wide range, by which the light diminishing ratio becomes greater. As to the cross-sectional configuration of the wire grid polarizer, when the polarized light polarizing along the groove direction of the wire grid polarizer enters, the wire grid polarizer blocks the polarized light, and when the polarized light polarizing perpendicular to the groove direction of the wire grid polarizer enters, the wire grid polarizer passes through the polarized light.

The polarizing filter layer 222 employing the wire grid structure has following features. The wire grid structure can be formed using known semiconductor manufacturing process. Specifically, a thin film of aluminum is deposited on a base, and then the patterning is performed, and the sub-wavelength convex/concave structure of the wire grid is formed by the metal etching. By using such manufacturing process, the long side direction of metal wire that is the polarization light direction (i.e., polarization axis) can be adjusted with a size of image capture pixel of the image sensor 206 such as several micron (μm) levels, with which transmission polarization axis can be selected with a unit of pixel. Further, since the wire grid structure can be formed of metal such as aluminum having a good level of heat resistance, the wire grid structure can be preferably employed for vehicles. The detail of the polarizing filter layer is described, for example, in JP-2014-32174-A.

Figure 8B:
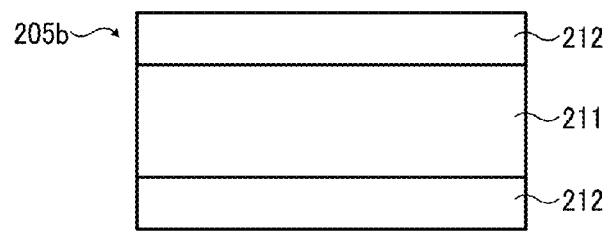
FIG. 8B illustrates a front view of the optical filter viewed from a side closer to an image sensor.
Figure 9:
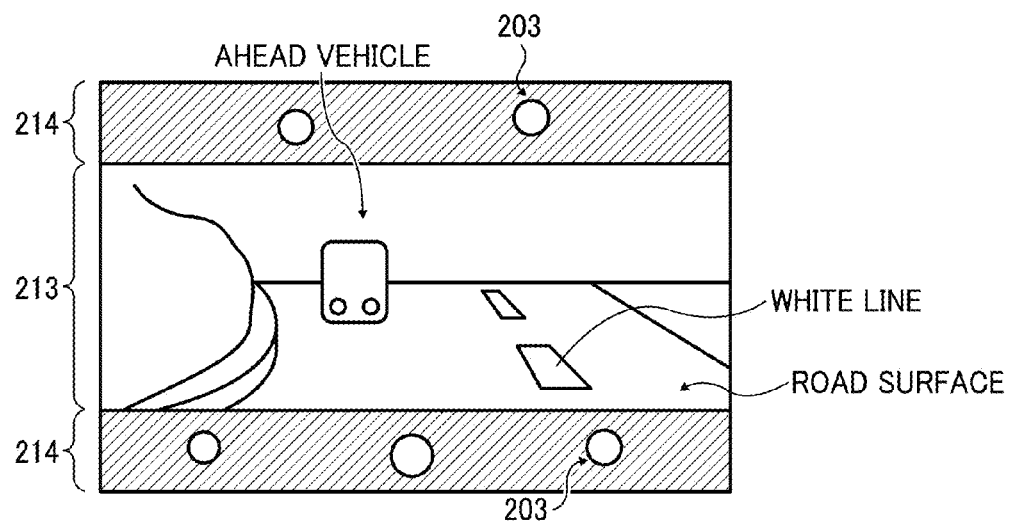
FIG. 9 illustrates an example of an image generated from captured image data.

FIG. 8B illustrates a front view of the optical filter 205 viewed from the side 205b closer to the image sensor 106. FIG. 9 illustrates an example of an image generated from captured image data. As illustrated in FIG. 8B, the optical filter 205 can be segmented into one filter area such as an infrared cut-filter area 211, and another filter area such as an infrared transmission filter 212. For example, the infrared cut-filter area 211 is disposed for a vehicle detection image area 213 that is at a center portion of one image capturing area having a height of a half (2/4) of the image capturing area while the infrared transmission filter 212 is disposed for a raindrop detection image area 214 that is at an upper one-fourth (¼) of one image capturing area and at a lower one-fourth (¼) of one image capturing area. The infrared transmission filter 212 can be devised by using the cut-filter (FIG. 6) or the band-pass filter (FIG. 7), in which the infrared transmission filter 212 can be used as a wavelength selection filter.

Typically, an image of headlight of the oncoming vehicle, an image of tail lamp of the front-running vehicle, and an image of the lane (e.g., white line) are present at the center of the image capturing area, an image of road surface, which exists in the front-direction and very close to the vehicle 100, is present at the lower part of the image capturing area, and an image of sky in the front-direction is present at the upper part of the image capturing area, Therefore, information required to recognize or identify the headlight of the oncoming vehicle, the tail lamp of the front-running vehicle, and the lane is present mostly in the center of the image capturing area, and thereby information present in the upper and lower parts of the image capturing area may not be relevant for recognizing the oncoming vehicle, the front-running vehicle, and the lane. Therefore, when an object detection process such as detecting the oncoming vehicle, the front-running vehicle, and the lane, and a raindrop detection are to be performed concurrently based on one captured image data, the upper and lower parts of the image capturing area can be used for the raindrop detection image area 214, and the center of the image capturing area can be used for the vehicle detection image area 213 by disposing the infrared transmission filter 212 at a corresponding position as illustrated in FIG. 9.

For example, as to the first example embodiment, the upper part and lower part of the image capturing area can be used as the raindrop detection image area 214, and the center and lower part of the image capturing area can be used as the vehicle detection image area 213. This configuration can preferably shorten a frame time of an image capturing frame used for the raindrop detection because the raindrop detection can be performed by using a smaller part of one image capturing area, and the exposure time for the raindrop detection can be set very short such as several micro seconds (μsec) to several hundreds micro seconds (μsec).

When the image capturing direction of the image capture device 200 is tilted to a downward direction, a hood or bonnet of the vehicle 100 may appear at the lower part of the image capturing area. In such a case, sun light or the tail lamp of the front-running vehicle reflected on the hood of the vehicle 100 becomes ambient light. If the ambient light is included in the captured image data, the headlight of the oncoming vehicle, the tail lamp of the front-running vehicle, and the lane may not be recognized correctly. In the first example embodiment, since the cut-filter (FIG. 6) or the band-pass filter (FIG. 7) can be disposed at a position corresponding to the lower part of the image capturing area, the ambient light such as sun light and the light of tail lamp of the front-running vehicle reflected from the hood can be removed. Therefore, the recognition precision of the headlight of the oncoming vehicle, the tail lamp of the front-running vehicle, and the lane can be enhanced.

Figure 10:
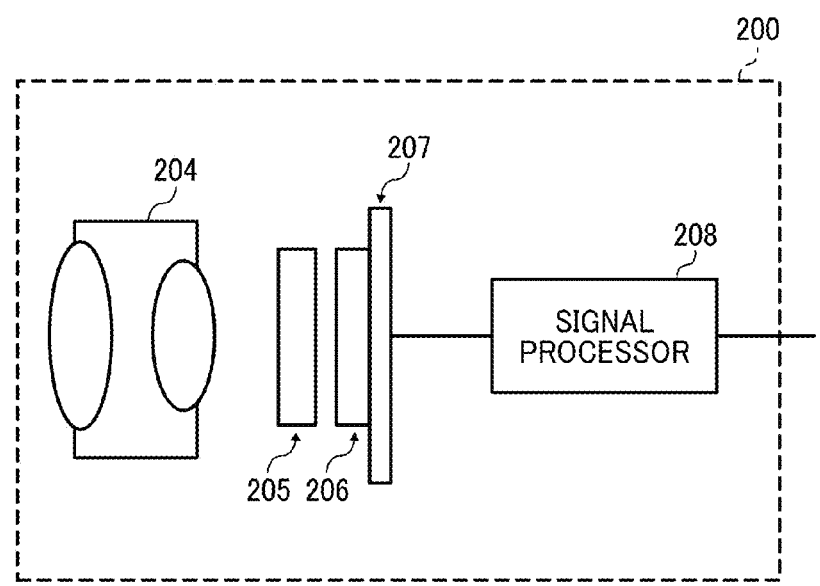
FIG. 10 illustrates a schematic configuration of the image capture device of the first example embodiment.

FIG. 10 illustrates a schematic configuration of the image capture device 200 of the first example embodiment. The image capture device 200 includes, for example, the capture lens 204, the optical filter 205, a sensor board 207, and a signal processor 208. The sensor board 207 is disposed with the image sensor 206 composed of a two-dimensional pixel array configured by arraying a number of light receiving elements in two dimensional directions. Each of light receiving elements of the image sensor 206 receives light having a given intensity or quantity, and the sensor board 207 outputs analog electrical signals corresponding to the received light intensity or quantity to the signal processor 208. Upon receiving the analog electrical signals, the signal processor 208 converts the analog electrical signals to digital electrical signals to generate and output the captured image data. Light coming from the image capturing area including one or more objects (detection-target object) passes the capture lens 204 and the optical filter 205, and then the image sensor 206 converts the received light to electrical signals based on the light intensity. When the signal processor 208 receives electrical signals such as analog signals output from the image sensor 206, the signal processor 208 converts the analog signals to digital signals including brightness or intensity data of each pixel on the image sensor 206 as the captured image data. The signal processor 208 outputs the captured image data to a later stage unit with horizontal/vertical synchronization signals of image.

Figure 11:
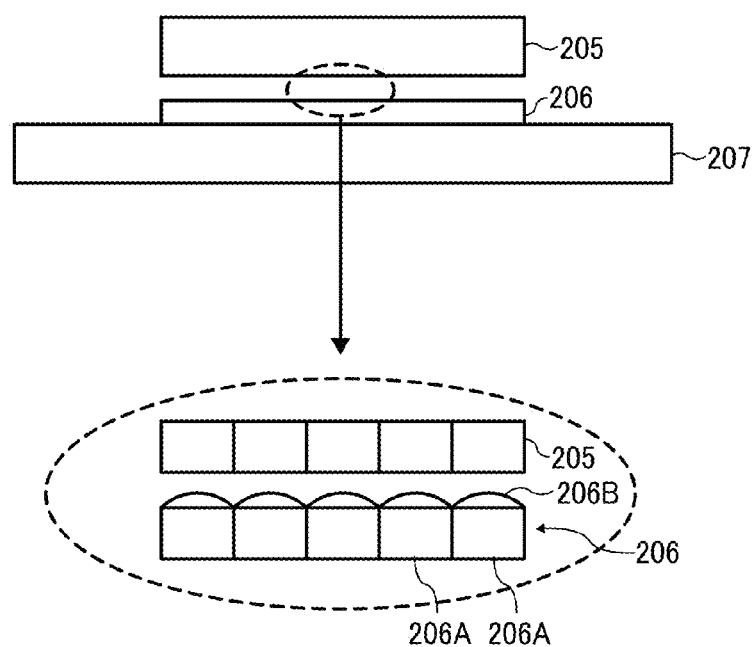
FIG. 11 illustrates a schematic configuration of the optical filter and the image sensor of the image capturing device viewed from a direction perpendicular to light passing or propagation direction.

FIG. 11 illustrates a schematic configuration of the optical filter 205 and the image sensor 206, viewed from a direction perpendicular to the light passing direction. Specifically, the image sensor 206 is a sensor employing, for example, a charge coupled device (CCD), a complementary metal oxide semiconductor (CMOS), or the like, and each of the light receiving elements of image sensor 206 is, for example, a photodiode 206A. The photodiodes 206A are arrayed as a two-dimensional array, in which each one of the photodiodes 206A corresponds to each one pixel. To enhance the light collection efficiency of the photodiode 206A, a micro lens 206B is disposed at the incidence side of the photodiode 206A. The image sensor 206 can be bonded to a printed wiring board (PWB) using known methods such as wire bonding to configure the sensor board 207. Hereinafter, the photodiode 206A may mean one photodiode or a plurality of photodiodes, and the photodiode 206A can be used as the light receiving element of the image sensor 206.

The image sensor 206 can be exposed by light using known exposure methods such as a global shutter method and a rolling shutter method. As to the global shutter method, light is received by all of the light receiving elements (photodiodes 206A) simultaneously (simultaneous exposure) and signals are read from each one of the light receiving elements. As to the rolling shutter method, light is received by one line composed of a given number of light receiving elements (photodiodes 206A) and then received by another one line composed of a given number of light receiving elements (photodiodes 206A) sequentially (line-by-line exposure), and signals are read from each one of the light receiving elements. The first example embodiment employs, for example, the rolling shutter method.

For example, the optical filter 205 and the image sensor 206 can be bonded, for example, using an ultra violet (UV) bonding agent, or the optical filter 205 and the image sensor 206 can be supported with each other by a spacer disposed therebetween at non-pixel areas not used for image capturing, and four sides of the optical filter 205 and the image sensor 206 can be bonded by UV bonding or heat bonding. By contacting the optical filter 205 and the image sensor 206 tightly, a boundary of the raindrop detection image area 214 and the vehicle detection image area 213 can be set clearly, with which the precision of raindrop detection can be enhanced.

In the first example embodiment, the adhering substance detection is performed to control operations of the wiper 107 and washer. The adhered substance is, for example, raindrop, bird droppings, splash (spray of water raised by other vehicles) or the like.

As to the light source 202, the angle of incident light emitted from the light source 202 and entering the windshield 105 is set with an angle that reflection light reflected at a boundary face of a raindrop and air can be captured by the image capture device 200. The intensity of reflection light reflected from the raindrop can become the greatest intensity when the light source 202 is disposed at a position substantially opposite to the light axis of the image capture device 200 with respect to the normal line of the windshield 105, or when the light axis of the light source 202 and the light axis of the image capture device 200 are set on the substantially same line. The intensity of reflection light reflected from the raindrop can become the smallest intensity when the normal line of the windshield 105 and the light axis of the light source 202 are aligned.

Further, the light source 202 can be disposed at a position that can irradiate light only to an area of the infrared transmission filter 212, with which a noise component from the vehicle detection image area 213 can be avoided. Further, the light source 202 can be disposed as a plurality of light sources 202. In this case, a polarizer pattern for each of areas of the polarizing filter layer 222 can be set a pattern that can pass through only a polarization light parallel to a face defined by the light axis of light emitted from one light source 202 to the windshield 105, emitting the greatest incident light intensity to the polarizer pattern, and the light axis of the capture lens 204.

The light emission of the light source 202 can employ a continuous emission method known as CW light emission or a pulse emission method that emits light with a specific time interval repeatedly. By synchronizing the light emission timing and image capturing timing, an effect of disturbance ambient light can be further reduced. When the plurality of the light sources 202 is disposed, the plurality of the light sources 202 can emit light simultaneously or sequentially. When the plurality of the light sources 202 emits the light sequentially, an effect of disturbance ambient light can be further reduced by synchronizing the light emission timing and image capturing timing.

Figure 12:
FIG. 12 is an experiment result of images that were captured when raindrops adhered
Figure 13:
FIG. 13 is an experiment result of images that were captured when no raindrops adhered.

FIGS. 12 and 13 show experiment results of images captured by the inventors. FIG. 12 is an experiment result when raindrops adhered, and FIG. 13 is an experiment result when no raindrops adhered, in which the lower part of image area is used as the raindrop detection image area 214.

Figure 14:
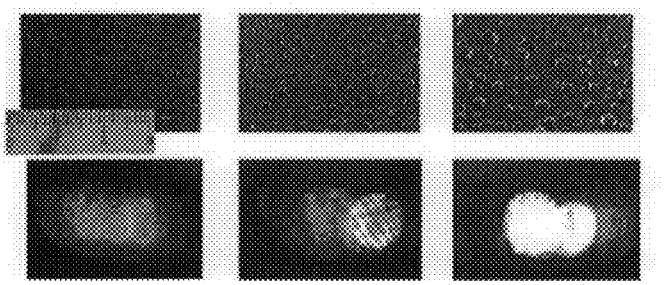
FIG. 14 shows expanded views of images captured for a raindrop detection image area by differentiating amount of raindrop.

FIG. 14 shows expanded views of images captured for the raindrop detection image area 214 by differentiating the amount of raindrop. When standard deviation of luminance of the captured images of FIG. 14 is computed, the standard deviation of luminance respectively becomes "20, 27, and 39" from left to right images of FIG. 14, and it is found that the standard deviation of luminance and the amount of raindrop have a correlation. Therefore, as to the first example embodiment, the image analyzer 102 computes values of the standard deviation of luminance for images captured for the raindrop detection image area 214, and measures the amount of raindrop based on the standard deviation of luminance. Further, instead of the standard deviation, variance can be used to measure the amount of raindrop.

A description is given of an image capturing operation of the image capture device 200 of the first example embodiment. The image capture device 200 captures object recognition frames and raindrop detection frames separately. The object recognition frames can be captured by receiving light coming from an area ahead of the vehicle 100. The object recognition frame is captured to obtain an image for an object recognition image area 213 used for recognizing one or more objects existing at the area ahead of the vehicle 100 (e.g., other vehicles, lanes, road surface, persons, obstacles). The raindrop detection frames can be captured by emitting the probe light-from the light source 202 to the windshield 105 and receiving light reflected from the windshield 105. The raindrop detection frame is captured to obtain an image for a raindrop detection image area 214 used for detecting raindrops adhering to the windshield 105. Specifically, one raindrop detection frame is captured after the object recognition frame is captured for a plurality of frames. The capturing of the raindrop detection frame and the object recognition frames are repeatedly performed as an image capturing operation.

Figure 15:
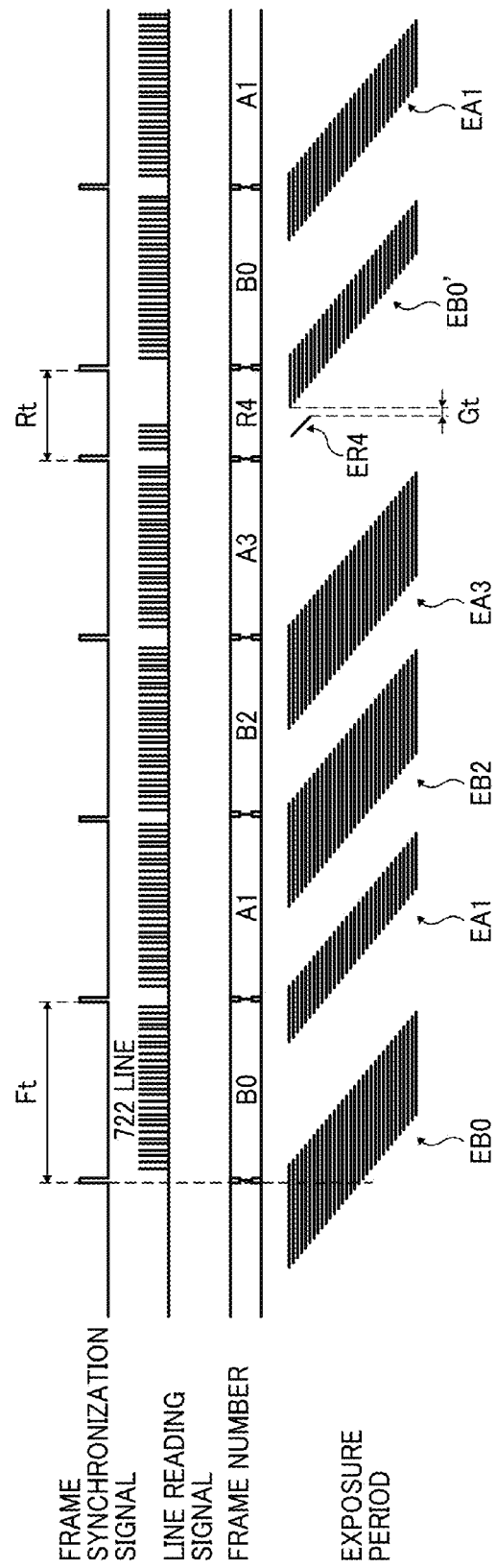
FIG. 15 is one example of a timing chart of an image capturing operation of the first example embodiment.

FIG. 15 is a timing chart of the image capturing operation of one example of the first example embodiment. FIG. 15 shows frame synchronization signals, line reading signals, frame numbers, exposure periods arranged along the same time line. As to the exposure period, the vertical direction corresponds to a position of each of light receiving element lines composing the image sensor 206. The received-light quantity of each of the light receiving elements of the image sensor 206 can be read and output for each of the light receiving elements in line with the corresponding line reading signal.

FIG. 16A indicates a relationship of data reading timing and exposure period for the sensing frames employing the rolling shutter method. FIG. 16B indicates a relationship of data reading timing and exposure period for the raindrop detection frames employing the rolling shutter method. The first example embodiment employs the rolling shutter method. As illustrated in FIG. 16A, as to the sensing frames, each timing of the line reading signal (horizontal synchronization signal) of each of the light receiving element lines " . . . , N, N+1, N+2, . . . " of the image sensor 206 is used as reference, in which the light-receiving start time, set based on the exposure time, is shifted for each of the light receiving element lines. As illustrated in FIG. 16B, as to the raindrop detection frame, each timing of the line reading signal (horizontal synchronization signal) of each of the light receiving element lines " . . . , M, M+1, M+2, . . . " of the image sensor 206 is used as reference, in which the light-receiving start time, set based on the exposure time, is shifted for each of the light receiving element lines. As to the first example embodiment, the image capturing operation is performed repeatedly as follows. Specifically, the sensing frames such as four object recognition frames B0 to A3 for acquiring images for the vehicle detection image area 213, and the raindrop detection frame such as one adhering detection frame R4 for acquiring an image for the raindrop detection image area 214 are captured sequentially, and this sequential capturing of the sensing frames and the raindrop detection frame are performed repeatedly.

In this description, an image capturing frame having a frame number B0 is a sensing frame used for a lane-keep control, which is known as Lane Departure Warning (LDW). The image capturing frame B0 corresponds to an automatic exposure frame, to which the exposure time during the image capturing operation is automatically controlled within a given time range. Specifically, a shorter exposure time is set for bright environment such as daytime, and a longer exposure time is set for dark environment such as night. The image capturing frame B0 is also referred as the sensing frame B0.

In this description, an image capturing frame having a frame number A1 is a sensing frame used for a light control of the headlight 104, which is known as Auto High Beam (AHB). The image capturing frame A1 corresponds to a locked-exposure frame, to which the exposure time during the image capturing operation is locked to a given value. The image capturing frame A1 is also referred as the sensing frame A1.

In this description, an image capturing frame having a frame number B2 is a sensing frame used for a collision-avoiding control, which is known as Front Collision Warning (FCW). The image capturing frame B2 corresponds to an automatic exposure frame, to which the exposure time during the image capturing operation is automatically controlled within a given time range. The image capturing frame B2 is also referred as the sensing frame B2.

In this description, an image capturing frame having a frame number A3 is a sensing frame used for a light control of the headlight 104 same as the image capturing frame A1 (second frame in FIG. 15). The image capturing frame A3 corresponds to a locked-exposure frame, to which the exposure time during the image capturing operation is locked to a given value. The image capturing frame A3 is also referred as the sensing frame A3.

In this description, an image capturing frame having a frame number R4 is a raindrop detection frame used for a drive control of the wiper 107. The image capturing frame R4 corresponds to a locked-exposure frame, to which the exposure time during the image capturing operation is locked to very short time such as several micro seconds ($\mu$sec) to several hundreds micro seconds ($\mu$sec). The raindrop detection frame used for acquiring an image of the raindrop detection image area 214 receives relatively strong light (high intensity light) from the light source 202. Therefore, a signal output from the image sensor 206 is saturated when the image sensor 206 receives the strong light. Therefore, the exposure time is preferably shortened as much as possible to prevent saturation of the signal output from the image sensor 206, and also to reduce the effect of ambient light not coming from the light source 202. Further, since the light intensity or quantity of the light emitted from the light source 202 is almost constant, the locked exposure time can be used for the image capturing frame R4.

As to the first example embodiment, the image capturing operation is performed by capturing the sensing frames such as B0 to A3 for a given times (e.g., seven times), and then capturing one raindrop detection frame R4, and this image capturing operation is repeatedly performed.

A description is given of a light emission control of the light source 202 of the first example embodiment. When an image is captured for the raindrop detection frame R4, the image can be captured by using the raindrop detection image area 214 alone. Therefore, when image data of the raindrop detection frame R4 is read, the image data is read from the light receiving element lines of the image sensor 206 corresponded to the raindrop detection image area 214, which means the light receiving element lines of the image sensor 206 corresponded to the upper part of the image capturing area is used to capture the image data for the raindrop detection frame R4. Therefore, when the image data is captured for the raindrop detection frame R4, the time period of emitting light from the light source 202 can be set in line with the exposure period of the light receiving element lines of the image sensor 206 corresponded to the raindrop detection image area 214.

During the time period emitting the light from the light source 202, the light emitted from the light source 202 may also enter a part of the image sensor 206 corresponding to the vehicle detection image area 213, and becomes disturbance ambient light for the vehicle detection image area 213. Therefore, the light emission control of the light source 202 is performed to emit the light from the light source 202 only for the exposure period of the light receiving element lines of the image sensor 206 corresponded to the raindrop detection image area 214. With this configuration, under a condition that the frame time of the raindrop detection frame R4 is set short, the light emitted light from the light source 202 does not become disturbance ambient light for the sensing frames A3 and B0 respectively right before and right after the raindrop detection frame R4 (FIG. 15).

FIG. 17 is an example of a timing chart of line reading signals for the raindrop detection frame R4 and the light emission timing of the light source 202. When an image is captured for the raindrop detection frame R4, the light source 202 can be controlled to emit the light continuously for the exposure period of the light receiving element lines of the image sensor 206 corresponded to the raindrop detection image area 214. In this configuration, image data can be acquired for the light receiving element lines of the image sensor 206 corresponded to the raindrop detection image area 214 under a condition that the light source 202 emits the light to all of the light receiving element lines of the image sensor 206 corresponded to the raindrop detection image area 214. However, if ambient light other than the probe light emitted from the light source 202 enters the image sensor 206, the image data captured by the image sensor 206 includes an error corresponding to the ambient light component.

Therefore, as to the first example embodiment, when capturing an image for one raindrop detection frame R4, the light emission control of the light source 202 is performed by setting at least one light-ON time of the light source 202, and one light-OFF time of the light source 202 during the exposure period of the light receiving element lines of the image sensor 206 corresponded to the raindrop detection image area 214. For example, as to the first example embodiment, the light emission control of the light source 202 is performed by setting the light-ON time of the light source 202 for one line, and the light-OFF time of the light source 202 for the next one line, and so on. Further, the light emission control of the light source 202 can be performed by setting the light-ON time of the light source 202 for two lines, and the light-OFF time of the light source 202 for the next two lines, and so on. The light emission timing of the light source 202 for each of the light receiving element lines of the image sensor 206 during the exposure period of the light source 202 can be set at a start timing of the exposure period of each light receiving element line as illustrated in FIG. 18, or an end timing of the exposure period of each light receiving element line as illustrated in FIG. 19.

A description is given of an experiment conducted by the inventors. In the experiment, similar to the first example embodiment, the light emission control of the light source 202 was performed by setting the light-ON time of the light source 202 for one light receiving element line, and the light-OFF time of the light source 202 for the next one light receiving element line for a plurality of light receiving element lines to check whether the raindrop detection can be performed effectively.

Figure 20:
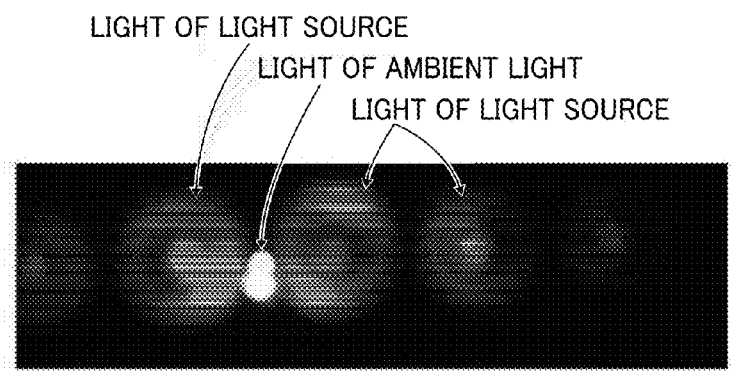
FIG. 20 is an example of image of the raindrop detection image area captured for the experiment, in which the light source was turned ON while ambient light enters.
Figure 21:
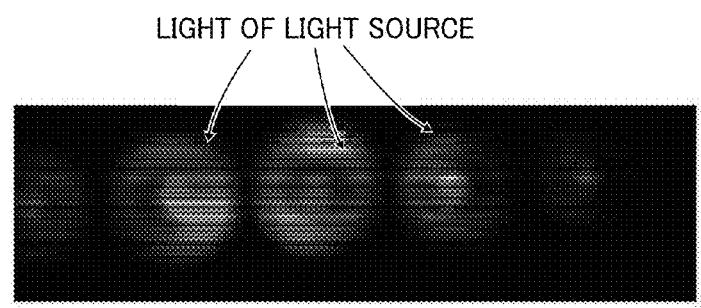
FIG. 21 is an example of image of the raindrop detection image area captured for an experiment, in which the light source was turned ON while ambient light did not enter.
Figure 22:
FIG. 22 is an expanded view of the image of FIG. 21 corresponding to an image portion where light emitted from the light source was captured.

FIG. 20 is an example of image of the raindrop detection image area 214 captured for an experiment, in which the light source 202 was turned ON while ambient light entered. FIG. 21 is an example of image of the raindrop detection image area 214 captured for the experiment, in which the light source 202 was turned ON while ambient light did not enter. FIG. 22 is an expanded view of the image of FIG. 21 corresponding to the image portion where the light emitted from the light source 202 was captured. As illustrated in FIG. 22, a high contrast can be obtained for each of light receiving element lines based on the light-ON time of the light source 202 for one light receiving element line, and the light-OFF time of the light source 202 for the next one light receiving element line.

When the light source 202 is turned OFF, the light emitted from the light source 202 is not received by the image sensor 206. Therefore, only the ambient light component is received by the image sensor 206. However, even if the total sum of pixel values of each light receiving element line (i.e., one line composed of light receiving elements in the image sensor 206) when the light source 202 is turned OFF is subtracted from the total sum of pixel values of each light receiving element line when the light source 202 is turned ON, the ambient light component cannot be removed completely, but some ambient light component still remains. Hereinafter, the ambient light component remaining after the subtraction may be referred to "remaining ambient light" for the simplicity of expression.

Specifically, when a difference between a value of the light receiving element line when the light source 202 is turned ON and a value of the light receiving element line when the light source 202 is turned OFF is computed, some ambient light component still remains because a position of the light receiving element line when the light source 202 is turned ON and a position of the light receiving element line when the light source 202 is turned OFF are different on the image sensor 206, which means the ambient light component included in the total sum of pixel values of the light receiving element line when the light source 202 is turned ON and the ambient light component included in the total sum of pixel values of the line when the light source 202 is turned OFF are received at different positions on the image sensor 206. Especially, when strong ambient light enters a part of the image sensor 206 as shown in FIG. 20, a light intensity profile in a spot of the ambient light on the image sensor 206 are almost uniform near the center of the spot, but the light intensity becomes smaller as closer to a periphery of the spot. Therefore, as to the ambient light at the periphery of the spot, a difference between light quantity (light intensity) of the ambient light when the light source 202 is turned ON and light quantity (light intensity) of the ambient light when the light source 202 is turned OFF becomes greater. Therefore, as to the light receiving element line corresponding to the ambient light at the periphery of the spot, even if the difference is obtained, the ambient light component cannot be removed completely, but a greater amount of ambient light component still remains.

Further, even if the global shutter method is employed, some ambient light component also remains even if the difference is obtained because a light-ON image and a light-OFF image captured by the global shutter method are captured as different frames. The light-ON image is captured when the light source 202 emits the light, and the light-OFF image is captured when the light source 202 does not emit the light. The image capturing timing of light-ON image and the image capturing timing of light-OFF image have a time difference corresponding to at least one frame time. Since the ambient light changes within a very short period of time, the ambient light may change during the period of time difference between the image capturing timing of light-ON image and image capturing timing of light-OFF image. In this case, the ambient light component included in the light-ON image does not equal to the ambient light component included in the light-OFF image, and thereby the ambient light component corresponding to the unequal amount still remains in the difference information.

If a greater amount of ambient light component still remains even if the difference is obtained, a detection error occurs to the raindrop detection processing, which is performed based on an assumption that the ambient light component is removed. Therefore, the remaining ambient light in the differential image causes error when the detection of adhering substance such as raindrop is performed. If the remaining amount of ambient light component in the differential image is stable within a given range, the detection error level of the adhering substance can be stable within a given range. When the raindrop detection processing is performed by using a detection result having the stable error level, the raindrop detection processing can be performed under an assumption that a pre-determined level of error is occurring, and thereby the raindrop detection processing may obtain a correct result of raindrop detection. However, the remaining amount of the ambient light component in the differential image may vary greatly depending on image capturing conditions, and fluctuate greatly. Therefore, the detection results of adhering substance such as raindrop fluctuate greatly. If the detection results fluctuate greatly, the raindrop detection processing that uses the fluctuated detection results cannot be performed under an assumption that the pre-determined level of error is occurring, in which the fluctuation of raindrop detection results may cause various problems. Therefore, the following raindrop detection processing is devised and performed as one example embodiment of the present invention.

Figure 23:
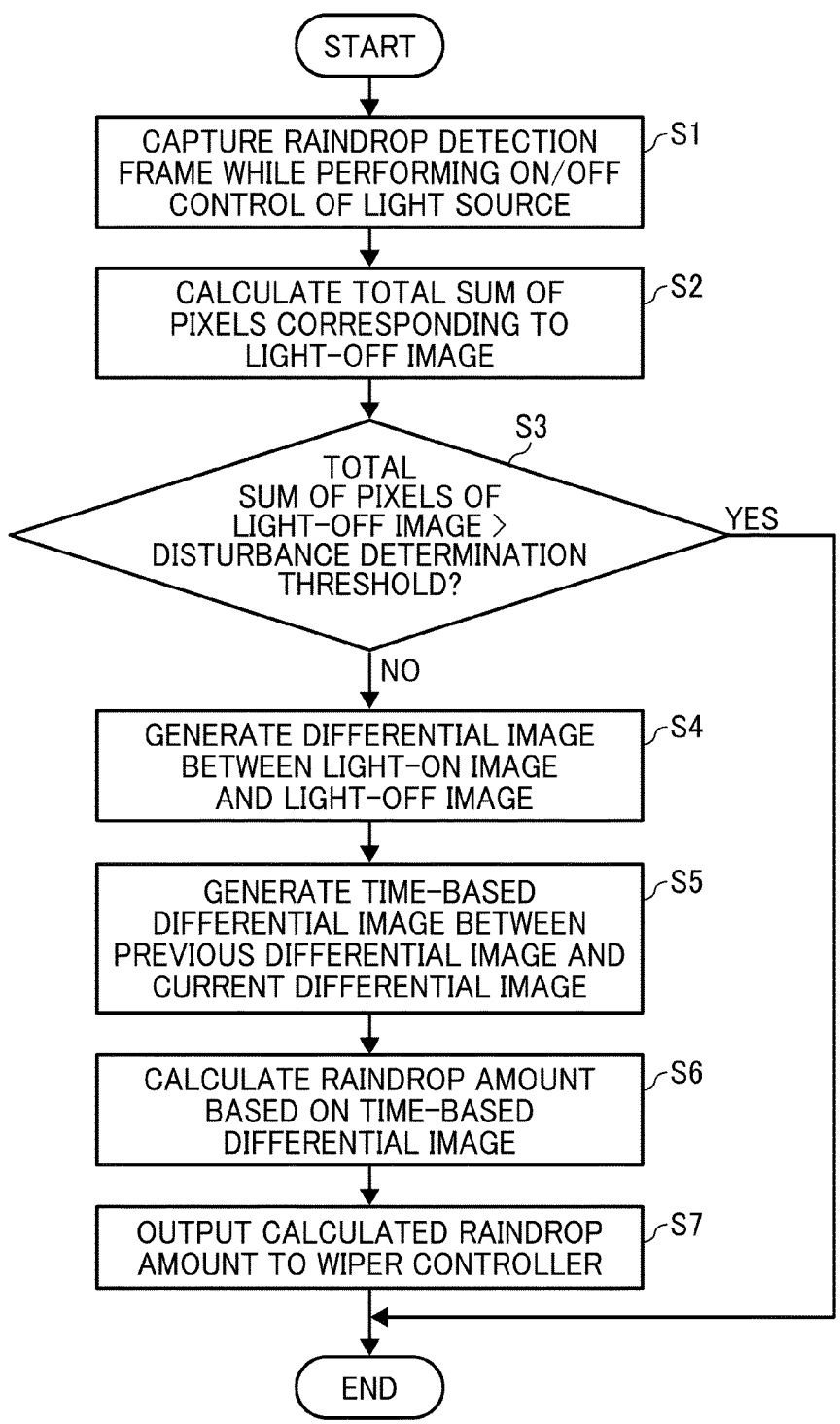
FIG. 23 is a flowchart showing the steps of raindrop detection processing of the first example embodiment.

FIG. 23 is a flowchart showing the steps of the raindrop detection processing of the first example embodiment. As indicated in FIG. 15, the image analyzer 102 performs an image capturing operation of the raindrop detection frame R4 while synchronizing the line reading signal in the raindrop detection frame R4 and the light emission timing of the light source 202 (S1). With this configuration, for example, an image of a raindrop detection image area alternately composed of imaging lines corresponding to the light-ON of the light source 202 and imaging lines corresponding to the light-OFF of the light source 202 along the upper-lower direction can be obtained as illustrated in FIG. 22. With this configuration, the light-ON image composed of imaging lines when the light source 202 is turned ON, and the light-OFF image composed of imaging lines when the light source 202 is turned OFF can be captured with one image capturing frame. Although FIG. 22 illustrates one example case that the light source 202 is controlled to set the light-ON lines and light-OFF lines alternately one by one line, but not limited hereto. For example, the light source 202 can be controlled to set one light-OFF line and a plurality of light-ON lines as one set.

Then, the image analyzer 102 computes the total sum of pixel values of the light-OFF image (total pixel values of light-OFF image) composed of lines when the light source 202 is turned OFF (S2). Then, the image analyzer 102 determines whether the computed total pixel values of light-OFF image is greater than a given threshold, which can be referred to a disturbance determination threshold (S3). In this configuration, the image analyzer 102 determines whether strong ambient light enters the image capture device 200 based on the total sum of pixel values, but not limited hereto. The image analyzer 102 can use any information to determine whether the strong ambient light enters the image capture device 200.

If the image analyzer 102 determines that the computed total pixel values of light-OFF image is less than the disturbance determination threshold (S3: NO), the image analyzer 102 generates a differential image between two images, in which the differential image is generated based on a differential value of pixel values between two images such as between pixel values of each of imaging lines when the light source 202 is turned ON and pixel values of each of imaging lines when the light source 202 is turned OFF, in which the imaging lines when the light source 202 is turned ON are adjacent to the imaging lines when the light source 202 is turned OFF (S4). The generated differential image data is stored in a memory. Then, the image analyzer 102 reads out previous data of differential image previously stored in the memory, and generates a time-based differential image between the previous differential image and current differential image based on a difference of the previous differential image and the current differential image (S5).

As to the first example embodiment, if an area in the time-based differential image has a pixel value greater than a given value, the area can be determined as an area that is adhered by raindrops, wherein raindrops did not adhere when the previous differential image was generated but raindrops adheres when the current differential image is generated. With employing the configuration of FIG. 23, when the raindrop is detected based on the pixel values of the time-based differential image, even if illuminance fluctuation occurs in a lighting area by the light source 202, illuminance becomes the same for the same portion of the previous differential image and the current differential image. Therefore, an effect of illuminance fluctuation to the detection precision of the raindrop 203 can be reduced, in particular prevented. Therefore, the raindrop 203 can be detected with an enhanced detection precision.

As to the first example embodiment, as above described, the light emitted from the light source 202 and then entering an adhering area on the windshield 105 where the raindrop 203 adheres can enter the image capture device 200 while the light emitted from the light source 202 and entering a non-adhering area on the windshield 105 where the raindrop 203 does not adhere does not enter the image capture device 200. Therefore, a raindrop image corresponding to the raindrop 203 can be generated on the raindrop detection image area 214 as a high luminance image. Therefore, a raindrop image area generated for the raindrop 203 has a greater pixel value in the time-based differential image.

The image analyzer 102 extracts an image area having a pixel value exceeding a given threshold from the time-based differential image, and identify the extracted image area as a candidate area of raindrop image area for generating the raindrop 203. Specifically, the image analyzer 102 compares the pixel value of the time-based differential image with the given threshold to perform the binarization processing. In the binarization processing, each of the pixels having a pixel value equal to or greater than the given threshold is assigned with "1," and each of the pixels having a pixel value less than the given threshold is assigned with "0" to generate a binarized image. Then, if a plurality of pixels assigned with "1" exists in a close range with each other in the binarized image, the plurality of close-ranged pixels are recognized as one image area, which means the labeling is performed. With this configuration, a collection of a plurality of close-ranged pixels having greater pixel values in the time-based differential image can be extracted as one image area.

Then, the image analyzer 102 performs a shape recognition process to the candidate area of raindrop image area, determined by the above described process, to identify a raindrop image area. Since the shape of a raindrop image in the captured image is typically circular, the image analyzer 102 performs the shape recognition process to the extracted candidate area of raindrop image area whether the shape of the extracted candidate area of raindrop image area is circular, and identifies the raindrop image area based on a result of the shape recognition process. Then, the image analyzer 102 computes or counts the number of the identified raindrop image areas as raindrop amount (S6).

The image analyzer 102 outputs the computed raindrop amount data to the wiper controller 106 (S7). The wiper controller 106 performs drive control of the wiper 107 and discharge control of washer liquid when the computed result of raindrop amount satisfies a give condition such as the counted value of raindrop amount is ten or more for all of twenty time-based differential images generated consecutively.

By contrast, if the total pixel values of light-OFF image exceeds the disturbance determination threshold (S3: YES), the image analyzer 102 ends the currently performed raindrop detection processing, and does not compute the raindrop amount due to the following reason.

Since the light-OFF image composed of lines when the light source 202 is turned OFF is an image captured by only capturing the ambient light, which is other than the light emitted from the light source 202, if the total pixel values of light-OFF image exceeds the disturbance determination threshold, it means that the strong ambient light enters the image capture device 200.

Under this situation, when an image of the raindrop detection image area is captured by switching the light-ON and light-OFF of the light source 202 for each of the lines by using the rolling shutter method, as above described, the ambient light component is included in the total pixel values of light-OFF image with a greater amount at the lines corresponding to the periphery of the spot of the strong ambient light. Therefore, the pixel value of the differential image is detected higher for the amount of the ambient light component. In this case, the pixel value of time-based differential image is also computed higher compared to a value not having an effect of the ambient light component, with which computation error of the raindrop amount occurs and as the wiper 107 is driven even if it is not raining.

As to the first example embodiment, since the raindrop amount is not computed when the total pixel values of light-OFF image exceeds the disturbance determination threshold, which means when the strong ambient light enters the image capture device 200, problems such as inappropriate operation of the wiper 107 can be prevented.

Further, as to the first example embodiment, if the strong ambient light continuously enters the image capture device 200, a time period of not computing the raindrop amount continues. If it starts to rain in this time period, a problem such as the wiper 107 is not driven even if it is raining may occur.

However, as to the first example embodiment, when an image of ahead of the vehicle 100 is captured through the windshield 105, the strong ambient light, corresponding to the total pixel values of light-OFF image exceeding the disturbance determination threshold, is mostly direct sun light, and/or sun light reflected from a bonnet of the vehicle 100. Since the strong ambient light caused by the sun light enters the image capture device 200, when the weather is fine such as sunny day, it is not raining. Therefore, even if the strong ambient light continuously enters the image capture device 200, and the time period of not computing the raindrop amount continues, the time period can be assumed that it is not raining with higher probability, and thereby no problems may not occur even if the raindrop detection is not performed in this time period.

As to the first example embodiment, when it is determined that the total pixel values of light-OFF image exceeds the disturbance determination threshold (S3: YES), it is controlled not to perform the steps S4 to S6 corresponding to the computing process of the raindrop amount, but the control method when it is determined that the total pixel values of light-OFF image exceeds the disturbance determination threshold is not limited hereto. For example, when it is determined that the total pixel values of light-OFF image exceeds the disturbance determination threshold (S3: YES), the computing process of the raindrop amount (i.e., S4 to S6) can be performed, and then, it can be controlled not to output a computation result of the raindrop amount to the wiper controller 106, with which problems caused by the computation error of the raindrop amount can be prevented.

Further, as to the first example embodiment, when it is determined that the total pixel values of light-OFF image exceeds the disturbance determination threshold (S3: YES), a computation result of the raindrop amount is not used for the wiper controller 106, but not limited hereto. For example, the computation result can be used by decreasing reliability of the computation result of raindrop amount. Specifically, the image analyzer 102 sets a level of reliability to each of the computation results of raindrop amount, in which the reliability level of the computation result of the raindrop amount is set lower as the total pixel values of light-OFF image becomes greater. Then, the image analyzer 102 outputs each of the computation results of raindrop amount to the wiper controller 106 with the set reliability. Then, the wiper controller 106 can control the wiper 107 depending on the level of reliability such as high to low levels, in which the wiper controller 106 can change a level of effect of the computation result of the raindrop amount to the controlling of the wiper 107, with which the wiper controller 106 can control the wiper 107 more effectively compared to a continuation that the computation result of the raindrop amount is not used completely when the total pixel values of light-OFF image exceeds the disturbance determination threshold.

Further, as to the first example embodiment, when the raindrop amount is computed, the time-based differential image is generated as a difference of the previous differential image and the current differential image, and then used for computing the raindrop amount. However, the time-based differential image may not be required for computing the raindrop amount in some cases. For example, an image area having a pixel value exceeding the given value is extracted from the current differential image, and then the extracted image area is identified as a candidate area of raindrop image area for generating the raindrop 203. Then, the shape recognition process is performed to the identified candidate area of raindrop image area to identify a raindrop image area, and then the number of identified raindrop image areas is counted, and the counted result is computed as the raindrop amount.

Further, the method of the raindrop detection processing is not limited to the above described method of the first example embodiment but other methods can be employed. For example, a simpler raindrop detection processing can be performed by determining whether the total sum of pixel values of the current differential image is a given threshold or more. When it is determined that the total sum of pixel values of the current differential image is the given threshold or more, it is determined that the raindrop amount exceeds a given value that activates the wiper 107, and then, the wiper controller 106 drives the wiper 107.

(Variant Example 1)

A description is given of one variant example of the raindrop detection processing of the first example embodiment. In the above described first example embodiment, the raindrop detection processing is performed by using the differential image generated by computing a difference of pixel values between the light receiving element lines when the light source 202 is turned ON and the light receiving element lines when the light source 202 is turned OFF. In variant example 1, the raindrop detection processing is performed by using only the light-ON image generated by using the image capturing lines when the light source 202 is turned ON without using the image capturing lines when the light source 202 is turned OFF.

Figure 24:
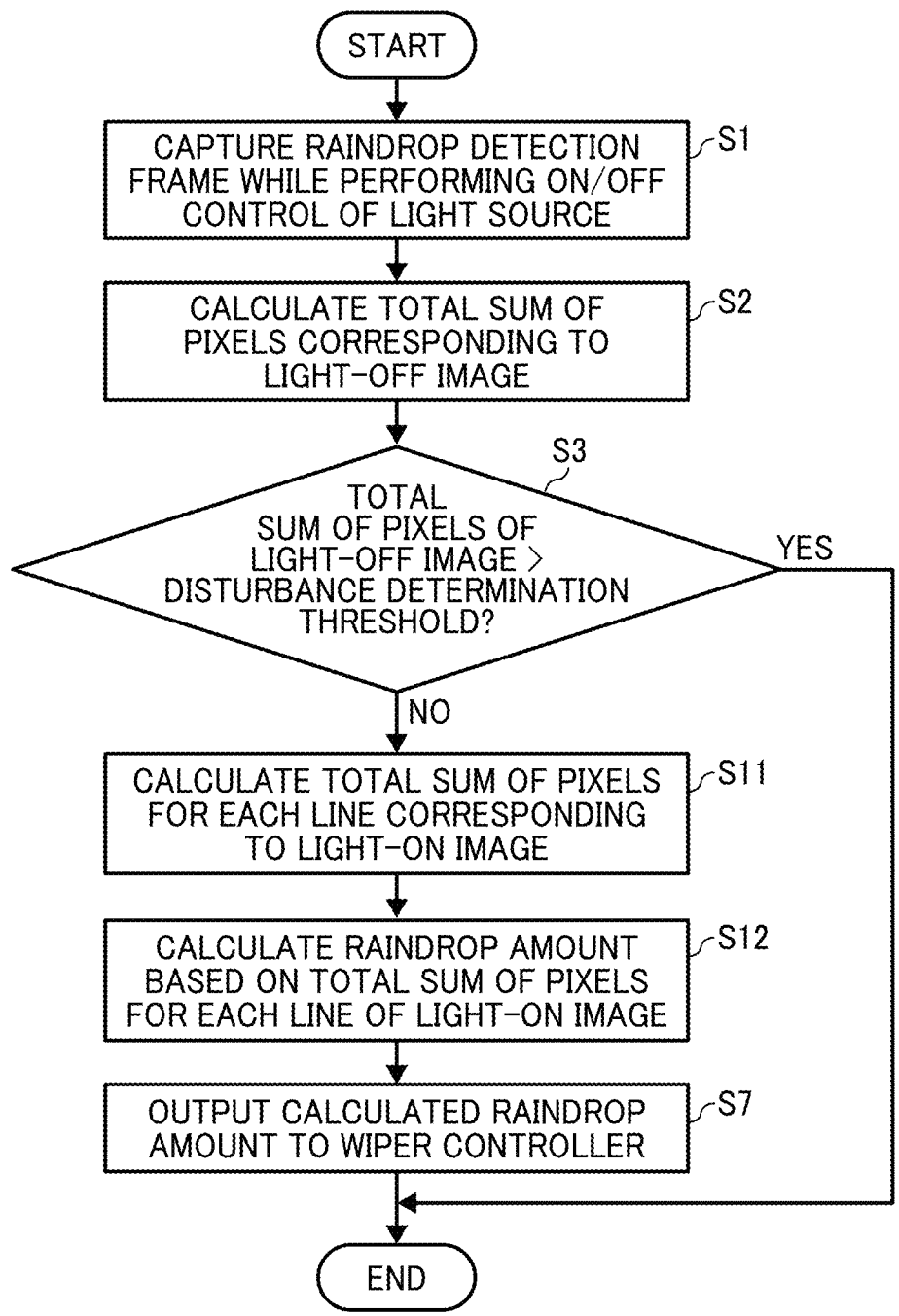
FIG. 24 is a flowchart showing the steps of raindrop detection processing of variant example 1.

FIG. 24 is a flowchart showing the steps of the raindrop detection processing of the variant example 1. In the variant example 1, the image analyzer 102 performs an image capturing operation of the raindrop detection frame R4 while synchronizing the line reading signal in the raindrop detection frame R4 and the light emission timing of the light source 202 (S1), and computes the total pixel values of light-OFF image (S2). Then, it is determined whether the total pixel values of light-OFF image exceeds the disturbance determination threshold (S3). In the variant example 1, if it is determined that the total pixel values of light-OFF image is less than the disturbance determination threshold (S3: NO), the image analyzer 102 computes the total sum of pixel values of each of the lines when the light source 202 is turned ON (S11) to compute the raindrop amount.

Then, the image analyzer 102 compares the total sum of pixel values for each of the lines when the light source 202 is turned ON and h a given threshold to identify the number of lines exceeding the given threshold, and computes the number of identified lines as the raindrop amount (S12). Then, the image analyzer 102 outputs the computed raindrop amount data to the wiper controller 106 (S7). The wiper controller 106 performs the drive control of the wiper 107 and discharge control of washer liquid. For example, when the computation result of the raindrop amount satisfies a given condition such as the counted values of raindrop amount is ten or more for all of twenty time-based differential images generated consecutively, the wiper controller 106 performs the drive control of the wiper 107 and discharge control of washer liquid.

In the variant example 1 too, if the total pixel values of light-OFF image exceeds the disturbance determination threshold (S3: YES), the image analyzer 102 ends the currently performed raindrop detection processing, and does not compute the raindrop amount. Therefore, similar to the above described first example embodiment, problems caused by the computation error of raindrop amount can be prevented.

As to the variant example 1, the number of lines having the total of pixel values exceeding the threshold is computed as the raindrop amount to perform the raindrop detection processing to devise a simplified method, but similar to the above described first example embodiment, the candidate area of raindrop image area can be identified, and the shape recognition processing is performed to the identified raindrop image area and then the raindrop amount is computed. Further, other methods can be used to compute the raindrop amount.

(Variant Example 2)

Figure 25:
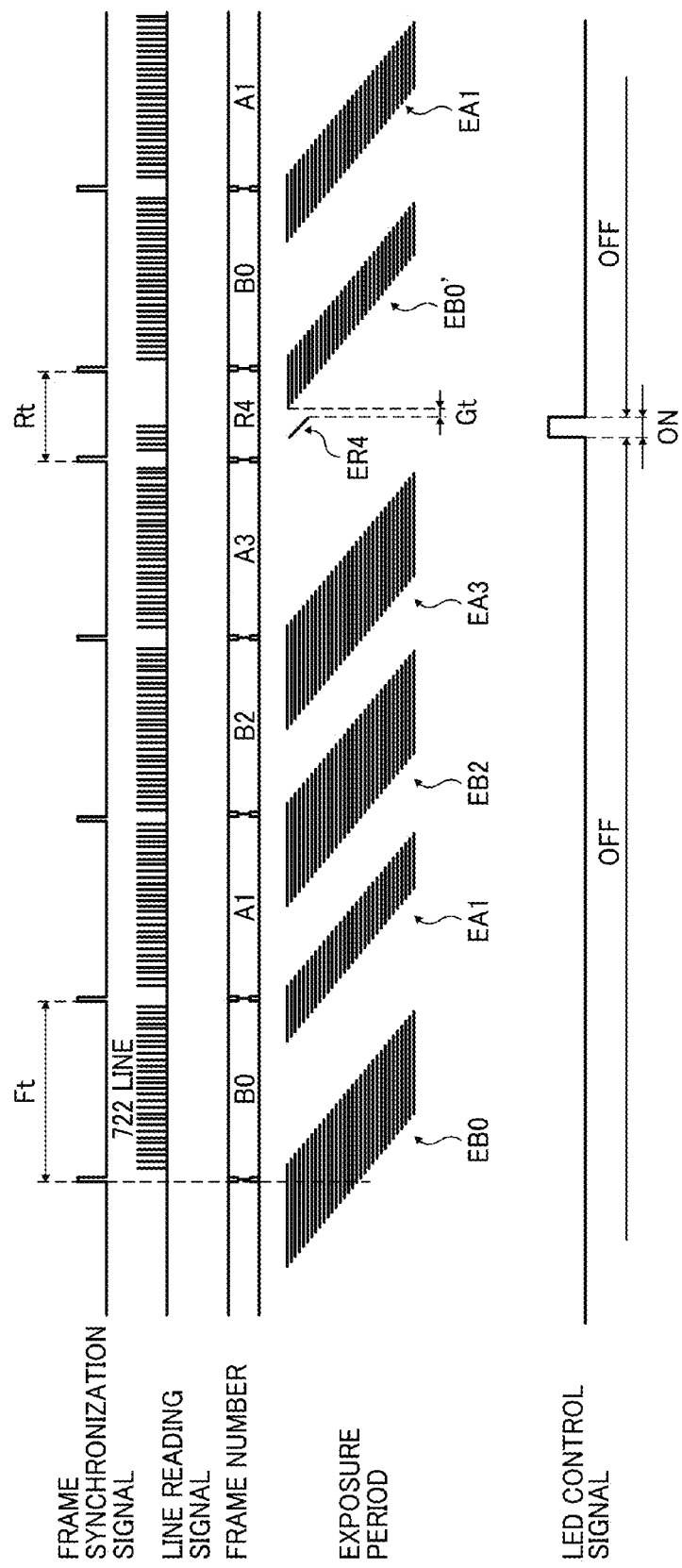
FIG. 25 is a timing chart of an image capturing operation and light emission control of a light source of variant example 2.

A description is given of another variant example of the first example embodiment employed for controlling the light source 202 and the raindrop detection processing. FIG. 25 is a timing chart of an image capturing operation and light emission control of the light source 202 of variant example 2. FIG. 25 shows frame synchronization signals, line reading signals, frame numbers, exposure periods, and LED control signals arranged along the same time line. The LED control signals are used to control the light-ON and light-OFF of the light source 202. The frame synchronization signals, line reading signals, frame numbers, and exposure periods in FIG. 25 is same as the above described first example embodiment shown in FIG. 15.

In the above described the first example embodiment, by synchronizing the line reading signals and the light emission timing of the light source 202 for the raindrop detection frame R4, an image of a raindrop detection image area alternately composed of the lines when the light source 202 is turned ON and the lines when the light source 202 is turned OFF arranged in the upper and lower direction is obtained from one raindrop detection frame R4. As to the variant example 2, as indicated in FIG. 25, the light source 202 is always turned ON during the exposure period of the raindrop detection frame R4, in which all lines are irradiated by the light emitted from the light source 202 when the raindrop detection frame R4 is captured.

As to the variant example 2, the light source 202 is always turned OFF during periods other than the exposure period of the raindrop detection frame R4. With this configuration, the light emission time of the light source 202 can be reduced, with which power saving of the light source 202 can be enhanced, dazzling of drivers of other vehicles caused by the light emitted from the light source 202 can be reduced and prevented, and disturbance to the vehicle detection image area 213 caused by the light emitted from the light source 202 can be prevented. Further, it should be noted that the light-OFF of the light source 202 is not always required during the periods other than the exposure period of the raindrop detection frame R4.

Figure 26:
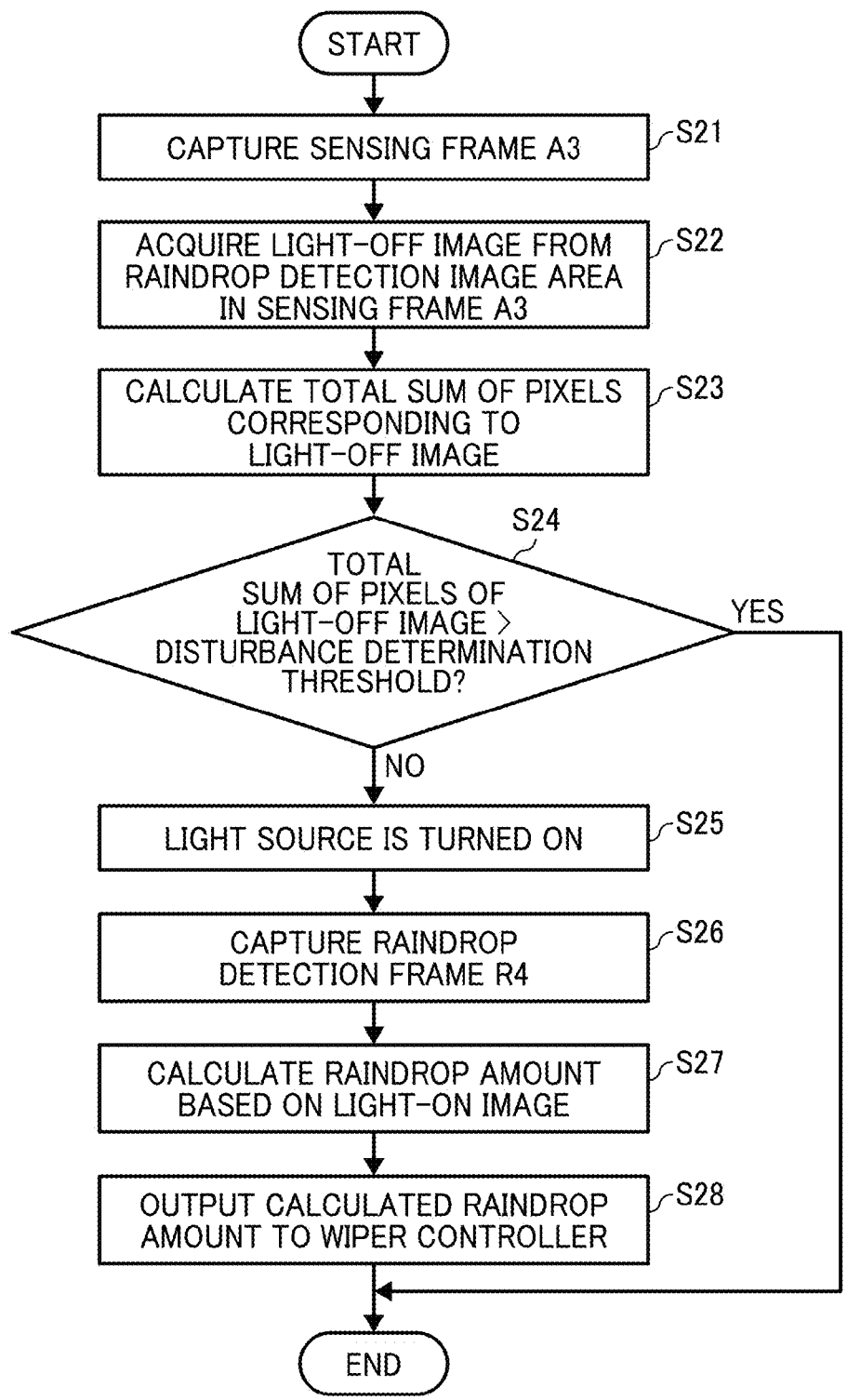
FIG. 26 is a flowchart showing the steps of the raindrop detection processing of variant example 2.

FIG. 26 is a flowchart showing the steps of the raindrop detection processing of the variant example 2. As to the variant example 2, the total pixel values of light-OFF image used for determining whether strong ambient light enters the image capture device 200 cannot be obtained from the raindrop detection frame R4 because the raindrop detection frame R4 is captured by always emitting the light from the light source 202. Therefore, the total pixel values of light-OFF image is required to be obtained from image data captured by not emitting the light from the light source 202.

For example, a first raindrop detection frame R4 is captured by always emitting the light from the light source 202, and a second raindrop detection frame R4 can be captured by not emitting the light from the light source 202 before or after the first raindrop detection frame R4, in which the total pixel values of light-OFF image can be obtained from image data of the raindrop detection image area obtained from the second raindrop detection frame R4.

Further, the sensing frames B0 to A3 captured by not emitting the light from the light source 202 before or after the raindrop detection frame R4 can be used to obtain image data of the raindrop detection image area, and then the total pixel values of light-OFF image can be obtained from the image data of the raindrop detection image area of the sensing frames B0 to A3 captured by not emitting the light from the light source 202.

Further, for example, the total pixel values of light-OFF image can be obtained from image data of another image area different from the raindrop detection image area, in which the total pixel values of light-OFF image can be obtained from the vehicle detection image area 213 or an image area other than the vehicle detection image area 213. In any cases, the obtained total pixel values of light-OFF image can be used effectively if an existence of strong ambient light component in the raindrop detection image area can be assumed with a given precision level or more based on the obtained total pixel values of light-OFF image. However, it is desirable that time difference between the image capturing timing of the image data used for obtaining the total pixel values of light-OFF image and the image capturing timing of the raindrop detection frame R4 used for computing the raindrop amount is smaller. Therefore, as to the variant example 2, the total pixel values of light-OFF image is obtained from image data of the raindrop detection image area captured in the sensing frame A3 that is set right before the raindrop detection frame R4 for computing the raindrop amount.

Specifically, the image analyzer 102 performs an image capturing operation of the sensing frame A3 under a condition that the light source 202 is turned OFF (S21), and extracts image data of the raindrop detection image area from the image data captured by the image capturing operation of the sensing frame A3 (S22). Then, the image analyzer 102 computes the total sum of pixel values of the extracted image data as the total pixel values of light-OFF image (S23).

Then, if it is determined that the total pixel values of light-OFF image does not exceed the disturbance determination threshold (S24: NO), the image analyzer 102 instructs the light source 202 to turn ON the light by synchronizing the light emission timing of the light source 202 with the exposure start timing of the first line of a next raindrop detection frame R4 (S25). Then, the image capturing operation is performed for the raindrop detection frame R4 (S26), Upon receiving the captured image data of the light-ON image for the raindrop detection image area from the image capture device 200, the image analyzer 102 computes the raindrop amount from the light-ON image (S27).

The computation of raindrop amount from the light-ON image can be performed as similar to the above described variant example 1. Specifically, the total of pixel values of each one of the lines corresponding to the raindrop detection frame R4 is computed, and then the computed total of pixel values of each one of the lines are compared with a given threshold to identify lines having the pixel value exceeding the threshold. Then, the identified number of the lines is computed as the raindrop amount. Further, as similar to the above described the first example embodiment, a candidate area of raindrop image area can be identified, and then the shape recognition processing is performed to the identified raindrop image area to compute the raindrop amount. Further, other methods can be used to compute the raindrop amount.

As to the variant example 2, if the total pixel values of light-OFF image exceeds the disturbance determination threshold (S24: YES), the image analyzer 102 ends the currently performed raindrop detection processing, and does not compute the raindrop amount. Therefore, similar to the above described first example embodiment, problems caused by the computation error of raindrop amount can be prevented.

Further, as to the variant example 2, if it is determined that the total pixel values of light-OFF image obtained from the sensing frame A3 exceeds the disturbance determination threshold (S24: YES), the light source 202 is not turned ON when an image capturing operation is performed for a next raindrop detection frame R4. Therefore, the light emission time of the light source 202 can be further reduced, with which the power saving can be enhanced.

As to the variant example 2, the total pixel values of light-OFF image used for determining whether the strong ambient light enters the image capture device 200 can be obtained from the sensing frame A3 captured right before the raindrop detection frame R4 used for computing the raindrop amount, but not limited hereto. For example, the total pixel values of light-OFF image can be obtained from the sensing frame B0 captured right after the raindrop detection frame R4 used for computing the raindrop amount, in which the computing of the raindrop amount by using captured image data of the light-ON image for the raindrop detection image area acquired by the image capturing operation of the raindrop detection frame R4 is always performed. Then, if the total pixel values of light-OFF image obtained from the sensing frame B0 captured right after the raindrop detection frame R4 does not exceed the disturbance determination threshold, the computation result of raindrop amount is output to the wiper controller 106. By contrast, if the total pixel values of light-OFF image obtained from the sensing frame B0 captured right after the raindrop detection frame R4 exceeds the disturbance determination threshold, the computation result of raindrop amount is not output to the wiper controller 106. With this controlling configuration, similar to the above described first example embodiment, problems caused by the computation error of raindrop amount can be prevented.

As to the variant example 2, the light source 202 is always turned ON during the exposure period of the raindrop detection frame R4, and the total pixel values of light-OFF image used for determining whether the strong ambient light enters the image capture device 200 is obtained from other image capturing frames different from the raindrop detection frame R4 by using the rolling shutter method. Further, instead of the rolling shutter method, the global shutter method can be used for the variant example 2 with the similar effect.

Figure 27:
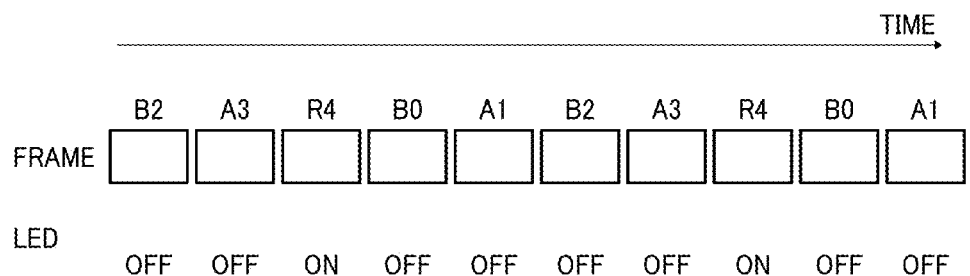
FIG. 27 is a schematics of light emission control of a light source of variant example 2 employing a global shutter method.

Specifically, when the global shutter method is employed, as illustrated in FIG. 27, the light source 202 is turned ON during the exposure period of the raindrop detection frame R4 to expose all pixels at the same time while the light source 202 is turned OFF during the exposure period of the mage capturing frames B0 to A3, which are other than the raindrop detection frame R4. Therefore, the total pixel values of light-OFF image used for determining whether the strong ambient light enters the image capture device 200 can be obtained from other image capturing frames such as the sensing frame A3 other than the raindrop detection frame R4 similar to the variant example 2.

(Second Example Embodiment)

A description is given of another device control system for controlling vehicle-mounted devices employing an adhering detection apparatus according to a second example embodiment. The second example embodiment employs a configuration almost same as the configuration of the first example embodiment and the variant examples except some parts of the image capturing apparatus 101. Therefore, different points of the second example embodiment are described.

Figure 28:
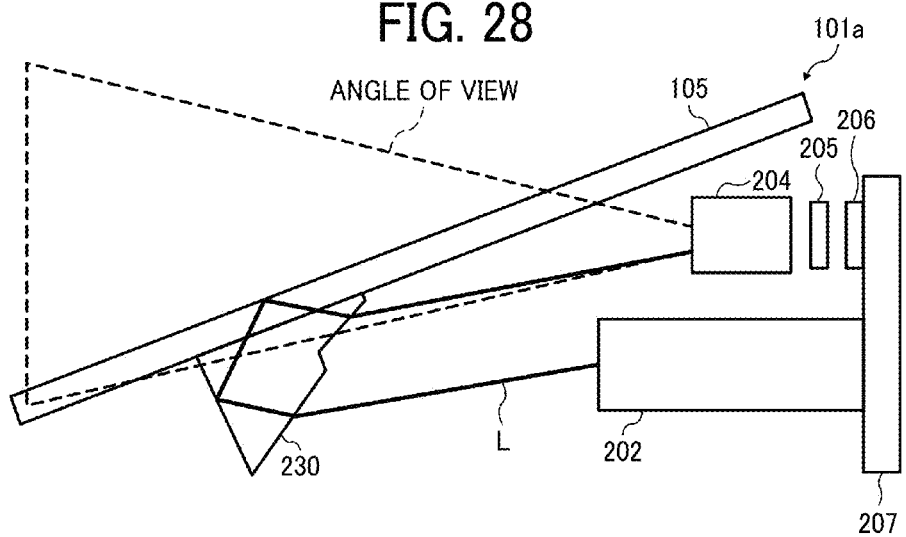
FIG. 28 is a schematic configuration of an image capturing apparatus of a second example embodiment.

FIG. 28 is a schematic configuration of an image capturing apparatus 101a of the second example embodiment that includes a prism 230, used as a reflective diffraction member, disposed on the inner face of the windshield 105. As to the image capturing apparatus 101a of the second example embodiment, as illustrated in FIG. 28, light L emitted from the light source 202 enters the prism 230 disposed on the inner face of the windshield 105, reflects totally on the outer face of the windshield 105 and enters the capture lens 204, and then the reflection light is received by the image sensor 206 disposed on the sensor board 207. Since the prism 230 is made of a material having a refractive index close to the refractive index of the windshield 105, the light emitted from the light source 202 can be reflected totally on the outer face of the windshield 105. The detail of the prism 230 is described, for example, in JP-2014-32174-A or the like.

By contrast, the light L emitted from the light source 202 passes through the outer face of the windshield 105 when the light L enters a portion of the outer face of the windshield 105 where a raindrop adheres, and thereby this light is not received by the image sensor 206. As to the above described first example embodiment, the light emitted from the light source 202 passes through the outer face of the windshield 105 where a raindrop does not adhere while the light emitted from the light source 202 reflects inside a raindrop adhering to the outer face of the windshield 105 and is then received by the image sensor 206.

Figure 29:
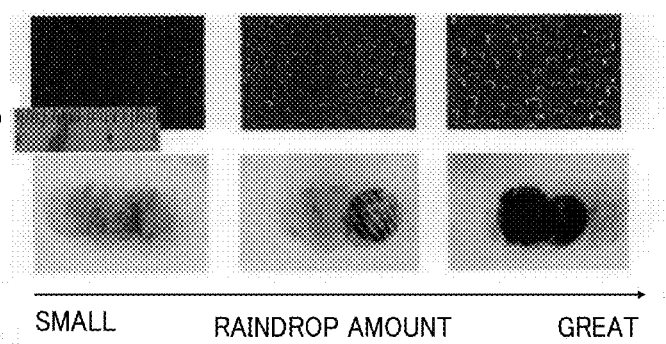
FIG. 29 is an expanded view of a raindrop detection image area used for detecting different amount of raindrop of the second example embodiment.

Therefore, the second example embodiment can obtain an image of the raindrop detection image area 214, which may appear as an inverse of an image of the raindrop detection image area 214 obtained for the first example embodiment. Specifically, as to the first example embodiment, an image having higher luminance can be obtained as a raindrop adhered portion as shown in FIG. 14, and as to the second example embodiment, an image having lower luminance can be obtained as a raindrop adhered portion as shown in FIG. 29. Therefore, as to the first example embodiment, the greater the total sum of pixel values, the greater the raindrop amount, whereas the second example embodiment, the smaller the total sum of pixel values, the greater the raindrop amount.

The above described example embodiments can be configured with following configurations.
(Configuration A)

In the above described example embodiments, the adhering detection apparatus includes, for example, the light source such as the light source 202 to emit probe light to the light translucent object such as the windshield 105 during an emission period, and to stop an emission of the probe light to the light translucent object during a non-emission period, the light receiver such as the image sensor 206 to receive light coming from the light translucent object, and the adhering detection processor such as the image analyzer 102 to perform an adhering detection processing (S26 and S27) for detecting a substance such as raindrop adhering to the light translucent object based on a level of light quantity of the light received by the light receiver, and to output a detection result of the adhering detection processing.

The adhering detection processor can determine whether the adhering detection processing is to be performed for the raindrop detection frame R4 based on a level of light quantity of the light received by the light receiver during the non-emission period of the light source 202. Specifically, the light source 202 does not emit the probe light during the exposure period of the sensing frame such as the sensing frame A3, which corresponds to the non-emission period of the light source 202. During the exposure period of the sensing frame A3, the light receiver receives the light with light quantity, which can be referred to the total pixel values of light-OFF image. Based on the total pixel values of light-OFF image, the adhering detection processor determines whether the adhering detection processing is to be performed for the raindrop detection frame R4 after the non-emission period, in which the exposure period of the raindrop detection frame R4 referred to the "scheduled emission period" because the light source 202 is expected to emit the probe light for capturing the raindrop detection frame R4 after capturing the sensing frame A3.

As above described, when the strong ambient light enters the light receiver, an effect of the ambient light component to the detection result to the adhering detection processing becomes greater. During the non-emission period, the light receiver receives only the ambient light. Therefore, based on a level of light quantity received by the light receiver during the non-emission period, it can estimate the level of the strong ambient light received by the light receiver. Therefore, based on the level of light quantity received by the light receiver during the non-emission period, it can estimate the level of the strong ambient light to be received by the light receiver during the scheduled emission period of the light source 202 after the non-emission period.

With this configuration, it can determine whether the estimated level of the ambient light to be occur in the scheduled emission period becomes the strong ambient light that affects the detection result of the adhering detection processing for the scheduled emission period greatly such as affecting the detection result by exceeding the allowable or acceptable level. If it is determined that the estimated level of the ambient light becomes the strong ambient light, it can be controlled not to perform the adhering detection processing. With this controlling configuration, among the detection results of the adhering detection processing to be used for the later stage processing and control (e.g., controlling of wiper 107), the detection results having the lower precision due to the strong ambient light are not used for the later stage processing and control. Therefore, the detection results used for the later stage processing and control can be prepared with the lower fluctuation of the precision. Therefore, problems to be occur in the later stage processing and control due to the greater fluctuation of the precision can be suppressed, or prevented.
(Configuration B)

As to the configuration A, the adhering detection apparatus includes the light source controller such as the image analyzer 102 to determine whether the probe light is emitted from the light source 202. The light source controller controls the light source 202 to stop an emission of the probe light for the scheduled emission period under a given condition. With this configuration, the light emission time of the light source 202 can be further reduced, with which the power saving can be enhanced.
(Configuration C)

In the above described example embodiments, the adhering detection apparatus includes, for example, the light source such as the light source 202 to emit the probe light to the light translucent object such as the windshield 105 during an emission period, and to stop an emission of the probe light to the light translucent object during a non-emission period, the light receiver such as the image sensor 206 to receive light coming from the light translucent object, and the adhering detection processor such as the image analyzer 102 to perform an adhering detection processing for detecting a substance such as raindrop adhering to the light translucent object based on a level of light quantity of the light received by the light receiver, and to output a detection result of the adhering detection processing. The adhering detection processor can determine whether the detection result of the adhering detection processing for the raindrop detection frame R4 corresponding the emission period set before or after the non-emission period is to be output based on a level of light quantity of the light received by the light receiver during the non-emission period of the light source 202 (i.e., total pixel values of light-OFF image).

With this controlling configuration, among the detection results of the adhering detection processing to be used for the later stage processing and control (e.g., controlling of wiper 107), the detection results having the lower precision due to the strong ambient light are not used for the later stage processing and control. Therefore, the detection results used for the later stage processing and control can be prepared with the lower fluctuation of the precision. Therefore, problems to be occur in the later stage processing and control due to the greater fluctuation of the precision can be suppressed, or prevented.

(Configuration D)

As to any one of the configurations A to C, when the level of light quantity (i.e., total pixel values of light-OFF image) received by the light receiver during the non-emission period exceeds a given threshold such as the disturbance determination threshold, the adhering detection processor determines that the adhering detection processing for the scheduled emission period is not performed, or a detection result of the adhering detection processing obtained for the emission period set before or after the non-emission period is not output. With this configuration, based on the given threshold set as required, it can detect the strong ambient light that affects the detection result of the adhering detection processing greatly such as affecting the detection result by exceeding the allowable or acceptable level.

(Configuration E)

In the above described example embodiments, the adhering detection apparatus includes, for example, the light source such as the light source 202 to emit the probe light to the light translucent object such as the windshield 105 during an emission period, and to stop an emission of the probe light to the light translucent object during a non-emission period, the light receiver such as the image sensor 206 to receive light coming from the light translucent object, and the adhering detection processor such as the image analyzer 102 to perform an adhering detection processing for detecting a substance such as raindrop adhering to the light translucent object based on a level of light quantity of the light received by the light receiver, and to output a detection result of the adhering detection processing. The adhering detection processor sets reliability to a detection result of the adhering detection processing, obtained for the emission period set before or after the non-emission period, at a lower level as a level of light quantity of the light received by the light receiver becomes greater during the non-emission period of the light source, and outputs the set reliability with the detection result.

With this configuration, the detection result of adhering substance can be used for the later stage processing and control with various ways in view of high to low levels of reliability, which means that the configuration E can perform the later stage processing and control more effectively compared to a configuration that the detection result having lower precision due to the strong ambient light is not used completely for the later stage processing and control.

(Configuration F)

As to any one of the configurations A to E, the adhering detection processor performs the adhering detection processing based on a level of light quantity of the light received by the light receiver during the emission period without using a level of light quantity of the light received by the light receiver during the non-emission period set before or after the emission period. With this configuration, the process of computing a difference of the light-ON image and the light-OFF image can be omitted, with which the adhering detection processing can be performed with a simplified method.

(Configuration G)

As to any one of the configurations A to E, the adhering detection processor performs the adhering detection processing based on difference information between a level of light quantity of the light received by the light receiver during the non-emission period set before or after the emission period, and a level of light quantity of the light received by the light receiver during the emission period. With this configuration, the adhering detection processing can be performed based on the difference information by excluding an effect of the ambient light component, with which the detection result of adhering substance having reduced the effect of the ambient light can be obtained.

(Configuration H)

As to any one of the configurations A to G, the light source emits the probe light having a specific wavelength range such as infrared wavelength range, and the light receiver is disposed with a wavelength selection filter such as the raindrop detection filter that passes the specific wavelength range, and blocks a wavelength range out of the specific wavelength range. The light receiver receives the light having the specific wavelength range via the wavelength selection filter.

With this configuration, the light quantity of the ambient light that enters the light receiver can be reduced, with which the detection result of adhering substance can be obtained by further reducing the effect of the ambient light. Further, by disposing the wavelength selection filter, the entering frequency of the strong ambient light to the light receiver can be reduced. With this configuration, the frequency of determination of not performing the adhering detection processing for the scheduled emission period, the frequency of determination of not outputting the detection result of the adhering detection processing, and the frequency of outputting the detection result having lower reliability can be reduced.

(Configuration I)

In the above described example embodiments, the device control system 1000 for controlling vehicle-mounted devices includes the adhering detection apparatus of any one of the configurations A to H to detect a substance adhering to the light translucent object; and one or more device controllers such as the wiper controller 106 to control one or more devices such as the wiper 107 mounted in a moveable apparatus such as the vehicle 100 based on a detection result detected by the adhering detection apparatus. With this configuration, the vehicle-mounted devices can be controlled effectively.

(Configuration J)

In the above described example embodiments, the carrier medium or a non-transitory computer-readable storage medium stores a program that, when executed by a computer, causes the computer such as the adhering detection processor to execute a method of detecting an adhering substance by using the adhering detection apparatus having any one of the configurations A to H. With this configuration, the later stage processing and control that use the detection result of adhering substance can be performed effectively, which means problems caused by the lower precision of the detection result of adhering substance can be suppressed.

(Configuration K)

In the above described example embodiments, the method of detecting an adhering substance includes the steps of emitting probe light from the light source 202 to the light translucent object 105 during an emission period of the light source, and not emitting the probe light from the light source during a non-emission period; receiving light coming from the light translucent object by a light receiver; detecting a substance adhering to the light translucent object based on a level of light quantity of the light received by the light receiver at the receiving step; outputting a detection result detected at the detecting step; and selectively performing a plurality of processes depending on a level of the light quantity of the light received by the light receiver during the non-emission period of the light source, in which it is determined whether the adhering detection processing is performed during a scheduled emission period of the light source, to be performed after the non-emission period, depending on the light quantity received by the light receiver during the non-emission period of the light source. With this configuration, the later stage processing and control that uses the detection result of adhering substance can be performed effectively by decreasing problems caused by the lower precision of the detection result of adhering substance.

(Configuration L)

In the above described example embodiments, the method of detecting an adhering substance includes the steps of emitting the probe light from the light source 202 to the light translucent object 105 during an emission period of the light source, and not emitting the probe light from the light source during a non-emission period; receiving light coming from the light translucent object by a light receiver; detecting a substance adhering to the light translucent object based on a level of light quantity of the light received by the light receiver at the receiving step; outputting a detection result detected at the detecting step; and selectively performing a plurality of processes depending on a level of the light quantity of the light received by the light receiver during the non-emission period of the light source, in which it is determined whether a detection result of the adhering detection processing for the emission period set before or after the non-emission period is output depending on a level of light quantity of the light received by the light receiver 206 during the non-emission period of the light source 202. With this configuration, the later stage processing and control that uses the detection result of adhering substance can be performed effectively by decreasing problems caused by the lower precision of the detection result of adhering substance.

(Configuration M)

In the above described example embodiments, the method of detecting an adhering substance includes the steps of: emitting probe light from the light source 202 to the light translucent object 105 during an emission period of the light source, and not emitting the probe light from the light source during a non-emission period; receiving light coming from the light translucent object by a light receiver; detecting a substance adhering to the light translucent object based on a level of light quantity of the light received by the light receiver at the receiving step; outputting a detection result detected at the detecting step; and selectively performing a plurality of processes depending on a level of the light quantity of the light received by the light receiver during the non-emission period of the light source, in which reliability is set to a detection result of the adhering detection processing, obtained for the emission period set before or after the non-emission period, at a lower level as a level of light quantity of the light received by the light receiver 206 becomes greater during the non-emission period of the light source 202, and outputs the set reliability with the detection result. With this configuration, the later stage processing and control that uses the detection result of adhering substance can be performed effectively by decreasing problems caused by the lower precision of the detection result of adhering substance.

The present invention can be implemented in any convenient form, for example using dedicated hardware platform, or a mixture of dedicated hardware platform and software. Each of the functions of the described embodiments may be implemented by one or more processing circuits or circuitry. Processing circuitry includes a programmed processor, as a processor includes circuitry. A processing circuit also includes devices such as an application specific integrated circuit (ASIC) and conventional circuit components arranged to perform the recited functions. For example, in some embodiments, any one of the information processing apparatus may include a plurality of computing devices, e.g., a server cluster, that are configured to communicate with each other over any type of communication links, including a network, a shared memory, etc. to collectively perform the processes disclosed herein.

The computer software can be provided to the programmable device using any storage medium or carrier medium such as non-volatile memory for storing processor-readable code such as a floppy disk, a flexible disk, a compact disk read only memory (CD-ROM), a compact disk rewritable (CD-RW), a digital versatile disk read only memory (DVD-ROM), DVD recording only/rewritable (DVD-R/RW), electrically erasable and programmable read only memory (EEPROM), erasable programmable read only memory (EPROM), a memory card or stick such as USB memory, a memory chip, a mini disk (MD), a magneto optical disc (MO), magnetic tape, a hard disk in a server, a flash memory, Blu-ray disc (registered trademark), secure digital (SD) card, a solid state memory device or the like, but not limited these. Further, the computer software can be provided through communication lines such as electrical communication line. Further, the computer software can be provided in a read only memory (ROM) disposed for the computer. The computer software stored in the storage medium can be installed to the computer and executed to implement the above described processing. The computer software stored in the storage medium of an external apparatus can be downloaded and installed to the computer via a network to implement the above described processing.

The hardware platform includes any desired kind of hardware resources including, for example, a central processing unit (CPU), a random access memory (RAM), and a hard disk drive (HDD). The CPU may be implemented by any desired kind of any desired number of processors. The RAM may be implemented by any desired kind of volatile or non-volatile memory. The HDD may be implemented by any desired kind of non-volatile memory capable of storing a large amount of data. The hardware resources may additionally include an input device, an output device, or a network device, depending on the type of apparatus. Alternatively, the HDD may be provided outside of the apparatus as long as the HDD is accessible. In this example, the CPU, such as a cache memory of the CPU, and the RAM may function as a physical memory or a primary memory of the apparatus, while the HDD may function as a secondary memory of the apparatus.

In the above-described example embodiment, a computer can be used with a computer-readable program, described by object-oriented programming languages such as C, C++, C#, Java (registered trademark), JavaScript (registered trademark), Perl, Ruby, or legacy programming languages such as machine language, assembler language to control functional units used for the apparatus or system. For example, a particular computer (e.g., personal computer, workstation) may control an information processing apparatus or an image processing apparatus such as image forming apparatus using a computer-readable program, which can execute the above-described processes or steps. In the above-described embodiments, at least one or more of the units of apparatus can be implemented as hardware or as a combination of hardware/software combination. Each of the functions of the described embodiments may be implemented by one or more processing circuits. A processing circuit includes a programmed processor, as a processor includes circuitry. A processing circuit also includes devices such as an application specific integrated circuit (ASIC) and conventional circuit components arranged to perform the recited functions.

Numerous additional modifications and variations for the communication terminal, information processing system, and information processing method, a program to execute the information processing method by a computer, and a storage or carrier medium of the program are possible in light of the above teachings. It is therefore to be understood that within the scope of the appended claims, the disclosure of the present invention may be practiced otherwise than as specifically described herein. For example, elements and/or features of different examples and illustrative embodiments may be combined each other and/or substituted for each other within the scope of this disclosure and appended claims.

What is claimed is:

1. An adhering detection apparatus comprising:
a light receiver to receive light coming from a light translucent object during an emission period, during which a light source is configured to emit light to the light translucent object, and a non-emission period of the light source, during which the light source is configured to stop emitting light to the light translucent object; and
an adhering detection processor to perform one or more processes to detect a substance adhering to the light translucent object based on a light quantity of the light coming from the light translucent object and received by the light receiver during the emission period, and to output a detection result of the adhering detection processing,
wherein the adhering detection processor performs the one or more processes upon a light quantity of ambient light received by the light receiver during the non-emission period of the light source failing to exceed the threshold, wherein the adhering detection processor is configured to set reliability to the detection result of the adhering detection processing, obtained for the emission period set before or after the non-emission period, at a relatively lower level as the light quantity of the light received by the light receiver becomes relatively greater during the non-emission period of the light source, and is configured to output the set reliability with the detection result.

2. The adhering detection apparatus of claim 1, wherein the adhering detection processor determines whether the one or more processes is performed during a scheduled emission period of the light source, scheduled after the non-emission period depending on the light quantity of the light received by the light receiver during the non-emission period of the light source failing to exceed the threshold.

3. The adhering detection apparatus of claim 2, further comprising a light source controller to control the emission period and the non-emission period of the light source,
wherein the light source controller is configured to selectively control the light source to stop the emission of the probe light during the scheduled emission period depending on the light quantity of the light received by the light receiver during the non-emission period of the light source failing to exceed the threshold.

4. The adhering detection apparatus of claim 2, wherein when the light quantity of the light received by the light receiver during the non-emission period exceeds a given threshold, the adhering detection processor stops the adhering detection processing for the scheduled emission period, or the adhering detection processor stops outputting the detection result of the adhering detection processing obtained for the emission period set before or after the non-emission period.

5. The adhering detection apparatus of claim 2, wherein the adhering detection processor is configured to perform the adhering detection processing based on the light quantity of the light received by the light receiver during the emission period without using the light quantity of the light received by the light receiver during the non-emission period set before or after the emission period.

6. The adhering detection apparatus of claim 2, wherein the adhering detection processor is configured to perform the adhering detection processing based on a difference between the light quantity of the light received by the light receiver during the non-emission period set before or after the emission period, and the light quantity of the light received by the light receiver during the emission period.

7. The adhering detection apparatus of claim 1, wherein the adhering detection processor is configured to whether the detection result of the adhering detection processing obtained for the emission period set before or after the non-emission period is output depending on the light quantity of the light received by the light receiver during the non-emission period of the light source failing to exceed the threshold.

8. A device control system for controlling one or more devices mounted in a vehicle comprising:
the adhering detection apparatus of claim 1 to detect a substance adhering to the light translucent object; and
one or more device controllers to control the one or more devices mounted in the vehicle based on a detection result detected by the adhering detection apparatus.

9. The device control system of claim 8, wherein the one or more device controllers include a windshield wiper controller.

10. An image capture apparatus, comprising:
the adhering detection apparatus of claim 1; and
the light source to emit light to a light translucent object during an emission period, and to stop an emission of the light to the light translucent object during a non-emission period.

11. A device control system for controlling one or more devices mounted in a vehicle comprising:
the image capture apparatus of claim 10 to detect a substance adhering to the light translucent object; and
one or more device controllers to control the one or more devices mounted in the vehicle based on a detection result detected by the adhering detection apparatus.

12. The device control system of claim 11, wherein the one or more device controllers include a windshield wiper controller.

13. The device control system of claim 11, further comprising a controller to alternate control of alternating elements of the light source between the emission and the non-emission periods.

14. The image capture apparatus of claim 10, further comprising a controller to alternate control of alternating elements of the light source between the emission and the non-emission periods.

15. An adhering detection apparatus, comprising:
a light receiver to receive light coming from a light translucent object during an emission period, during which a light source is configured to emit light to the light translucent object, and a non-emission period of the light source, during which the light source is configured to stop emitting light to the light translucent object; and
an adhering detection processor to perform one or more processes to detect a substance adhering to the light translucent object based on a light quantity of the light coming from the light translucent object and received by the light receiver during the emission period, and to output a detection result of the adhering detection processing, wherein the adhering detection processor performs the one or more processes upon a light quantity of ambient light received by the light receiver during the non-emission period of the light source failing to exceed the threshold, and wherein the adhering detection processor determines whether the one or more processes is performed during a scheduled emission period of the light source, scheduled after the non-emission period depending on the light quantity of the light received by the light receiver during the non-emission period of the light source failing to exceed the threshold; and
a wavelength selection filter to pass light having a first wavelength range, and to block light having a second wavelength range out of the first wavelength range,
wherein the light source is configured to emit the light having the first wavelength range,
wherein the light receiver is configured to receive the probe light having the first wavelength range emitted from the light source and reflected from the light translucent object via the wavelength selection filter.

16. A device control system for controlling one or more devices mounted in a vehicle comprising:
the adhering detection apparatus of claim 15 to detect a substance adhering to the light translucent object; and
one or more device controllers to control the one or more devices mounted in the vehicle based on a detection result detected by the adhering detection apparatus.

17. An image capture apparatus, comprising:
the adhering detection apparatus of claim 15; and
the light source to emit light to a light translucent object during an emission period, and to stop an emission of the light to the light translucent object during a non-emission period.

18. A device control system for controlling one or more devices mounted in a vehicle comprising:
the image capture apparatus of claim 17 to detect a substance adhering to the light translucent object; and
one or more device controllers to control the one or more devices mounted in the vehicle based on a detection result detected by the adhering detection apparatus.

19. A method of detecting a substance adhering to a light translucent object, the method comprising:
receiving, by a light receiver, light coming from a light translucent object during an emission period, during which a light source is configured to emit light to the light translucent object, and during a non-emission period during which the light source is configured to stop emitting light to the light translucent object;
detecting a substance adhering to the light translucent object based on a light quantity of the light received by the light receiver during the emission period;
outputting a detection result obtained based upon the detecting; and
performing one or more processes upon a light quantity of ambient light received by the light receiver during the non-emission period of the light source failing to exceed a threshold, wherein the detecting of the substance adhering to the light translucent object includes setting a reliability to the detection result, obtained for the emission period set before or after the non-emission period, at a relatively lower level as the light quantity of the light received by the light receiver becomes relatively greater during the non-emission period of the light source, and wherein the outputting includes outputting the set reliability with the detection result.

20. A non-transitory computer-readable storage medium storing a program that, when executed by a computer, causes the computer to execute a method of detecting a substance adhering to a light translucent object by using an adhering detection apparatus, the method comprising of:
receiving, by a light receiver, light coming from a light translucent object during an emission period, during which a light source is configured to emit light to the light translucent object, and during a non-emission period during which the light source is configured to stop emitting light to the light translucent object;
detecting a substance adhering to the light translucent object based on a light quantity of the light received by the light receiver during the emission period;
outputting a detection result obtained based upon the detecting; and
performing one or more processes upon a light quantity of ambient light received by the light receiver during the non-emission period of the light source failing to exceed a threshold, wherein the detecting of the substance adhering to the light translucent object includes setting a reliability to the detection result, obtained for the emission period set before or after the non-emission period, at a relatively lower level as the light quantity of the light received by the light receiver becomes relatively greater during the non-emission period of the light source, and wherein the outputting includes outputting the set reliability with the detection result.

* * * * *